US011191707B2

(12) United States Patent
Pressly et al.

(10) Patent No.: US 11,191,707 B2
(45) Date of Patent: *Dec. 7, 2021

(54) METHODS FOR TREATING RELAXED HAIR

(71) Applicant: Olaplex, Inc., Boston, MA (US)

(72) Inventors: Eric D. Pressly, Santa Barbara, CA (US); Craig J. Hawker, Santa Barbara, CA (US)

(73) Assignee: OLAPLEX, INC., Boston, MA (US)

( * ) Notice: Subject to any disclaimer, the term of this patent is extended or adjusted under 35 U.S.C. 154(b) by 132 days.

This patent is subject to a terminal disclaimer.

(21) Appl. No.: 16/571,933

(22) Filed: Sep. 16, 2019

(65) Prior Publication Data

US 2020/0009035 A1    Jan. 9, 2020

Related U.S. Application Data

(60) Continuation of application No. 15/626,453, filed on Jun. 19, 2017, now abandoned, which is a continuation of application No. 15/341,893, filed on Nov. 2, 2016, now Pat. No. 9,717,668, which is a division of application No. 15/137,788, filed on Apr. 25, 2016, now Pat. No. 9,597,273.

(60) Provisional application No. 62/152,220, filed on Apr. 24, 2015.

(51) Int. Cl.
| *A61K 8/46* | (2006.01) |
| *A61K 8/19* | (2006.01) |
| *A61K 8/36* | (2006.01) |
| *A61K 8/362* | (2006.01) |
| *A61K 8/41* | (2006.01) |
| *A61Q 5/04* | (2006.01) |
| *A45D 7/04* | (2006.01) |
| *A61Q 5/02* | (2006.01) |
| *A61Q 5/12* | (2006.01) |
| *A45D 7/00* | (2006.01) |

(52) U.S. Cl.
CPC ............... *A61K 8/416* (2013.01); *A45D 7/00* (2013.01); *A45D 7/04* (2013.01); *A61K 8/19* (2013.01); *A61K 8/36* (2013.01); *A61K 8/362* (2013.01); *A61K 8/41* (2013.01); *A61K 8/46* (2013.01); *A61K 8/466* (2013.01); *A61Q 5/02* (2013.01); *A61Q 5/04* (2013.01); *A61Q 5/12* (2013.01); *A61K 2800/59* (2013.01); *A61K 2800/882* (2013.01); *A61K 2800/884* (2013.01)

(58) Field of Classification Search
CPC ............... A45D 7/00; A61K 2800/59; A61K 2800/882; A61K 2800/884; A61K 8/19; A61K 8/362; A61K 8/46; A61K 8/36; A61K 8/41; A61K 8/466; A61Q 5/04; A61Q 5/02; A61Q 5/12; A61Q 5/04

See application file for complete search history.

(56) References Cited

U.S. PATENT DOCUMENTS

| 2,850,351 A | 9/1958 | Moore |
| 3,142,623 A | 7/1964 | Zviak |
| 3,472,243 A | 10/1969 | Wall |
| 3,568,685 A | 3/1971 | Scott |
| 3,840,656 A | 10/1974 | Kalopissis |
| 4,067,345 A | 1/1978 | Kelly |
| 4,138,478 A | 2/1979 | Reese |
| 4,240,450 A | 12/1980 | Grollier |
| 4,425,132 A | 1/1984 | Grollier |
| 4,532,950 A | 8/1985 | Lang |
| 4,567,039 A | 1/1986 | Stadnick |
| 4,793,993 A | 12/1988 | Siuta-Mangano |
| 4,812,307 A | 3/1989 | Siuta-Mangano |
| 4,834,971 A | 5/1989 | Klenk |
| 5,143,518 A | 9/1992 | Madrange |
| 5,221,286 A | 6/1993 | Singleton |
| 5,350,572 A | 9/1994 | Savaides |
| 5,356,438 A | 10/1994 | Kim |
| 5,490,980 A | 2/1996 | Richardson |
| 5,565,216 A | 10/1996 | Cowsar |
| 5,651,960 A | 7/1997 | Chan |
| 5,656,265 A | 8/1997 | Bailey |
| 5,811,085 A | 9/1998 | Halloran |

(Continued)

FOREIGN PATENT DOCUMENTS

| DE | 1220969 | 7/1966 |
| DE | 4300320 | 7/1994 |

(Continued)

OTHER PUBLICATIONS

Examination Report PH (Philippines) 1-2016-500132, dated Oct. 29, 2019.
Fragrance Journal, 49-56 (Jan. 1997).
Imai, et al., "The Dyeing Mechanism of Oxidative Hair Color in White and Black Human Hair", J. Soc. Cosmet. Chem. Jpn., 44 (3):208-215 (2010) with English Abstract.
Japan Cosmetic Industry Association ed., 1st Ed., Japan Cosmetic Industry Association, 139-142 (2012).
Joko, et al., "A Tentative Mechanism of Oxidative Dyeing for Keratin Fibers", J. Soc. Cosmet. Chem. Jpn., 42 (3):185-200 (2008) with English Abstract.

(Continued)

*Primary Examiner* — Abigail Vanhorn
(74) *Attorney, Agent, or Firm* — Pabst Patent Group LLP

(57) ABSTRACT

Methods and kits for treating hair or preventing damage in the relaxing of hair are disclosed herein. Hair that is damaged during a relaxing treatment with hydroxide-containing relaxing agents, can be treated with formulations containing one or more active agents. The active agent formulations can be applied simultaneously with the hair relaxing formulation, or optionally applied immediately following application of the relaxing formulation, to reduce damage and breakage. Use of the active agent formulation along with a relaxing treatment can be used to control the level of curl achieved or retained in the relaxed hair, as compared to the natural amount of curl in the untreated hair.

18 Claims, No Drawings

(56) References Cited

U.S. PATENT DOCUMENTS

| | | |
|---|---|---|
| 5,833,966 A | 11/1998 | Samain |
| 6,010,690 A * | 1/2000 | Varco .................. A61P 17/16 |
| | | 424/70.13 |
| 6,173,717 B1 | 1/2001 | Schonert |
| 6,358,502 B1 | 3/2002 | Tanabe |
| 6,458,906 B1 | 10/2002 | Torgerson |
| 6,537,532 B1 | 3/2003 | Torgerson |
| 6,706,258 B1 | 3/2004 | Gallagher |
| 6,984,250 B1 | 1/2006 | Legrand |
| 7,041,142 B2 | 5/2006 | Chan |
| 7,044,986 B2 | 5/2006 | Ogawa |
| 7,179,302 B2 | 2/2007 | Baswell |
| 7,390,479 B2 | 6/2008 | Sockel |
| 7,597,880 B2 | 10/2009 | Gyamfi |
| 7,598,213 B2 | 10/2009 | Geary |
| 8,137,414 B2 | 3/2012 | Wood |
| 8,298,519 B2 | 10/2012 | Adams |
| 8,556,992 B2 | 10/2013 | De George |
| 8,613,913 B2 | 12/2013 | Chang |
| 9,095,518 B2 * | 8/2015 | Pressly .................. A61K 8/0216 |
| 9,144,537 B1 * | 9/2015 | Pressly .................. A61K 8/22 |
| 9,180,086 B2 | 11/2015 | Cabourg |
| 9,326,926 B2 | 5/2016 | Pressly |
| 9,498,419 B2 | 11/2016 | Pressly |
| 9,597,273 B2 | 3/2017 | Pressly |
| 9,668,954 B2 | 6/2017 | Pressly |
| 9,713,583 B1 | 7/2017 | Pressly |
| 9,717,668 B2 * | 8/2017 | Pressly .................. A45D 7/04 |
| 9,855,447 B2 | 1/2018 | Pressly |
| 9,872,821 B1 | 1/2018 | Pressly |
| 10,076,475 B2 | 9/2018 | Gershon |
| 10,076,478 B2 | 9/2018 | Pressly |
| 2001/0042276 A1 | 11/2001 | Kawasoe |
| 2002/0189034 A1 | 12/2002 | Kitabata |
| 2002/0197227 A1 | 12/2002 | Scholz |
| 2003/0037384 A1 | 2/2003 | Nguyen |
| 2003/0049222 A1 | 3/2003 | Akhter |
| 2003/0072962 A1 | 4/2003 | Matsuzaki |
| 2004/0034944 A1 | 2/2004 | Legrand |
| 2004/0034946 A1 | 2/2004 | Legrand |
| 2004/0086475 A1 | 5/2004 | Boswell |
| 2004/0088800 A1 | 5/2004 | Cotteret |
| 2005/0036970 A1 | 2/2005 | Sabbagh |
| 2005/0087718 A1 | 4/2005 | Okada |
| 2005/0193501 A1 | 9/2005 | Chan |
| 2006/0024257 A1 | 2/2006 | Chang |
| 2006/0228316 A1 | 10/2006 | Cannell |
| 2007/0041921 A1 | 2/2007 | Neill |
| 2007/0067924 A1 | 3/2007 | Beck |
| 2007/0141005 A1 | 6/2007 | Jonathan |
| 2007/0261594 A1 | 11/2007 | Vaskelis |
| 2007/0264208 A1 | 11/2007 | Mougin |
| 2008/0066773 A1 | 3/2008 | Anderson |
| 2008/0138309 A1 | 6/2008 | Malle |
| 2008/0141468 A1 | 6/2008 | Cotteret |
| 2008/0187506 A1 | 8/2008 | Carballada |
| 2009/0022681 A1 | 1/2009 | Carballada |
| 2009/0126756 A1 | 5/2009 | Syed |
| 2009/0252697 A1 | 10/2009 | Barbarat |
| 2010/0004391 A1 | 1/2010 | Haddleton |
| 2010/0015253 A1 | 1/2010 | Nigel |
| 2010/0202998 A1 | 8/2010 | Ramos-Stanbury |
| 2011/0038818 A1 | 2/2011 | William |
| 2011/0097293 A1 | 4/2011 | Gary |
| 2011/0250153 A1 | 10/2011 | Owen |
| 2011/0256084 A1 | 10/2011 | Dixon |
| 2012/0024309 A1 | 2/2012 | Pratt |
| 2012/0114584 A1 | 5/2012 | Uyi |
| 2012/0145477 A1 | 6/2012 | Scott |
| 2012/0148517 A1 * | 6/2012 | Gilmore .................. A61K 8/24 |
| | | 424/70.4 |
| 2012/0180807 A1 | 7/2012 | Flohr |
| 2012/0244082 A1 | 9/2012 | Sulzbach |
| 2013/0034515 A1 | 2/2013 | Stone |
| 2013/0152959 A1 | 6/2013 | Genain |
| 2013/0172518 A1 | 7/2013 | Huang |
| 2013/0309190 A1 | 11/2013 | Dimotakis |
| 2013/0340785 A1 * | 12/2013 | Baum .................. A61K 8/4913 |
| | | 132/206 |
| 2014/0125452 A1 | 5/2014 | Josefiak |
| 2014/0186283 A1 | 7/2014 | Cabourg |
| 2014/0196741 A1 | 7/2014 | Cabourg |
| 2015/0034117 A1 | 2/2015 | Pressly |
| 2015/0034119 A1 | 2/2015 | Pressly |
| 2015/0297496 A1 | 10/2015 | Kroon |
| 2015/0320658 A1 * | 11/2015 | Flohr .................. A61K 8/8152 |
| | | 132/209 |
| 2015/0328102 A1 | 11/2015 | Pressly |
| 2016/0081899 A1 | 3/2016 | Pressly |
| 2016/0193129 A1 | 7/2016 | Pressly |
| 2016/0263003 A1 | 9/2016 | Pressly |
| 2016/0310394 A1 | 10/2016 | Pressly |

FOREIGN PATENT DOCUMENTS

| | | |
|---|---|---|
| DE | 10051773 | 4/2002 |
| DE | 10051774 | 4/2002 |
| DE | 102004052480 | 5/2006 |
| DE | 202015104742 | 10/2015 |
| EC | 993171 | 10/1999 |
| EC | 055712 | 3/2005 |
| EP | 0299764 | 1/1989 |
| EP | 0298684 | 4/1993 |
| EP | 0609796 | 8/1994 |
| EP | 0978272 | 2/2000 |
| EP | 1174112 | 1/2002 |
| EP | 1726289 | 11/2006 |
| EP | 1779896 | 5/2007 |
| EP | 2295029 | 3/2011 |
| EP | 2478892 | 7/2012 |
| FR | 1356138 | 3/1964 |
| FR | 1356139 | 3/1964 |
| FR | 2975900 | 12/2012 |
| GB | 713675 | 8/1954 |
| GB | 741307 | 11/1955 |
| GB | 773559 | 4/1957 |
| GB | 1125794 | 8/1968 |
| GB | 1260451 | 1/1972 |
| GB | 1584364 | 2/1981 |
| JP | H02138110 | 5/1990 |
| JP | 2006327994 | 12/2006 |
| JP | 2009007283 | 1/2009 |
| JP | 2010155823 | 7/2010 |
| KR | 830002888 | 12/1983 |
| KR | 20010039848 | 7/2001 |
| KR | 1020030003970 | 1/2003 |
| KR | 20040098688 | 11/2004 |
| KR | 1020060059564 | 6/2006 |
| WO | 9300882 | 1/1993 |
| WO | 9308787 | 5/1993 |
| WO | 9501152 | 1/1995 |
| WO | 1997024106 | 7/1997 |
| WO | 2000032158 | 6/2000 |
| WO | 2001047486 | 7/2001 |
| WO | 2002032383 | 4/2002 |
| WO | 2002032386 | 4/2002 |
| WO | 02074272 | 9/2002 |
| WO | 2006011771 | 2/2006 |
| WO | 2006051248 | 5/2006 |
| WO | 2008/072672 | 6/2008 |
| WO | 2008072672 | 6/2008 |
| WO | 2009024936 | 2/2009 |
| WO | 2010049434 | 5/2010 |
| WO | 2011134785 | 11/2011 |
| WO | 2012084532 | 1/2012 |
| WO | 2012164064 | 1/2012 |
| WO | 2012080321 | 6/2012 |
| WO | 2012122457 | 9/2012 |
| WO | 2014016407 | 1/2014 |
| WO | 2014118212 | 8/2014 |
| WO | 2014125452 | 8/2014 |
| WO | 2014167508 | 10/2014 |
| WO | 2014207097 | 12/2014 |
| WO | 2015017768 | 2/2015 |

(56) References Cited

FOREIGN PATENT DOCUMENTS

| WO | 2015026994 | 2/2015 |
|---|---|---|
| WO | 2015175986 | 11/2015 |
| WO | 2016207840 | 12/2016 |
| WO | 2017041908 | 3/2017 |

OTHER PUBLICATIONS

L'Oreal vs. Olaplex Judgement UK 2019 EWCA CIV 1943, dated Nov. 18, 2019.
Office Action BR (Brazil) 112016026378-2 dated Oct. 15, 2019, with English Summary.
Office Action Japanese Appeal No. 2018-15999; JP (Japan) 2016-572832 date Nov. 19, 2019 with English Translation.
Third Party Observation EA (Eurasia) 201692315, dated Sep. 13, 2019, with English Translation.
Third Party Observation EP (Europe) 15725209.9 dated Nov. 29, 2019.
Third Party Observation EP (Europe) 15725209.9 filed Nov. 15, 2019.
Amazon.com Joico Vero K Pak Veroxide Developer Cream 32 ounce Beauty, filed Jan. 29, 2019.
Amended Statement of Case on Validity (Olaplex) REDACTED Version filed Nov. 6, 2017.
Aparecida Da Franca, et al., "Types of Hair Dye and Their Mechanisms of Action", Cosmetics 2, 110-126, 2015.
Asquith, et al., Chemistry of Natural Protein Fibers (1977).
Australian Examination Report Examination Report AU2015058904 dated Nov. 2, 2016.
B(l)ack to blonde article, behindthechair.com accessed Jan. 1, 2019.
Barradas, et al., "The hydrolysis of maleimide in alkaline solution", Can. J. Chem, 54, 1400-1404 (1976).
Berth and Reese, "Veranderung des haarkeratins durch kosmetische behandlung und naturliche umwelteinflusse", J Soc Cos Chem., 15:659-66 (1964).
Bolduc, C. et al., "Hair Care Products: Waving, Straightening, Conditioning, and Coloring" Clinics in Dermatology 19:431-436 (2001).
Borish Declaration—REDACTED version of Exhibit 2025, dated Oct. 20, 2017 (Exhibit 2049) filed in PGR 2017-00012.
Borish, Edward T.—Declaration, signed Oct. 18, 2017 (REDACTED, non-confidential version).
Borish, Edward T.—Deposition transcript, pp. 1-204, Jan. 5, 2018.
Borish, Edward T. CV filed Nov. 16, 2018.
Bouillon and Wilkinson, Chapter 1, "Hair Structure, Function, and Physicochemical Properties" in The Science of Hair Care, (2005).
Bouillon and Wilkinson, Chapter 12, "Hair Structure, Function, and Physicochemical Properties" in The Science of Hair Care, (2005).
Brown and Pohl, "Permanent Hair Dyes", Society of Cosmetic Chemists, 1-41, (1996).
Brown, Excerpts from the 5th Edition of Organic Chemistry, (2011).
Brown, Hair Coloring, Clairol, Inc., Stamford, Connecticut (1997).
Canadian Office Action 2,947,303 dated Dec. 28, 2016.
Canadian Protest Application 2,947,303 mailed Feb. 8, 2017.
Canari, "Effect of pH on Dicarboxylic Acids Extraction by Amine-Based Extractants", Ind. Eng. Chem. Res., 42:1293-1300 (2003).
Catzy Blonde Statement of the use of Maleic Acid, dated Dec. 1, 2017.
Central Role Presentation, dated Jan. 26, 2015.
Chan, "Nucleophile-Initiated Thiol-Michael Reactions: Effect of Organocatalyst, Thiol, and Ene", Macromolecule, 13:6381-6388 (2010).
Christal, Dean—Declaration, signed Oct. 18, 2017(REDACTED) filed in PGR 2017-00012.
Chromastics, "The evolution of hair color", Technical ad training manual, pp. 1-32 (2009).
CIR Safety Report "Final Report on the Safety Assessment of Maleic Acid", International Journal of Toxicology, 26 (Suppl.2); 125-131, (2007).
Citraconic Acid, C5H604-PubChem, accessed Dec. 21, 2018.
Combined Search and Examination Report for GB 1523109.5 dated Feb. 4, 2016.
Combined Search and Examination Report GB 1618423.6 dated Nov. 29, 2016.
Combined Search report and Examination Report in connection with UK patent application, GB1513932.2 dated Sep. 24, 2015.
Corbett, et al., "Hair Colorants: Chemistry and toxicology", Cosmetic Science Monographs, (1998).
CTFA Cosmetic Ingredient handbook, pp. 1023-1 thru 1023-8, John Wenninger Editor, (1992).
Davies and Evans, "The isomerization of maleic acid in aqueous solutions", Transections of Faraday Society, 52:74-80 (1956).
Davis, et al., Excerpts from Modern Chemistry, pp. 214, 215, and 454 (1999).
Declaration of Arun Nandagiri dated Jan. 30, 2017, with curriculum vitae.
Declaration of Arun Nandagiri dated Jan. 31, 2017, with curriculum vitae.
Declaration of Edward T. Borish in Support of Olaplex's Motion for a Preliminary Injunction, filed Jan. 18, 2017, with curriculum vitae.
Defendant-Intervenor brief in Appeal No. 2019Heo3618, KR (Korea) 1787310, dated Oct. 23, 2019.
Defendant's Brief—REDACTED version—in Opposition to Plaintiff's Motion for Preliminary Injunction, by L'Oréal USA Products, Inc., et al., filed in Liqwd, Inc. et al. v. L'Oreal USA, Inc. et al., U.S. District Court for the District of Delaware, Civil Action No. 1:17-cv-00014 on Apr. 17, 2017.
Dispenza License status webpage, https://aca.licensecenter.ny.gov/aca/GeneralProperty/LicenseeDetail, retrieved from the internet Dec. 12, 2017.
Dispenza, Thomas—Declaration, signed Oct. 17, 2017 filed in PGR 2017-00012.
Dispenza, Thomas—Deposition transcript, pp. 1-125, Dec. 13, 2017.
Dmuchovsky, et al., "The Mechanism of the Base-Catalyzed Addition of Thiols to Maleic Anhydride", Free-Radical Addition of Thiols to Maleic Anhydride, 86:2875-2877 (1964).
Doering, et al., "Super mild oxidation coloring: preventing hair damage at the molecular lever", IFSCC Magazine, 10(4):323-9 (2007).
Dombrink and Tanis "pH & hair shampoo," Chem Matters, 8 (1983).
E-mail correspondence regarding documentary evidence as provided by the third party (EX 36), filed May 16, 2018.
Engel, et al., "Fumaric acid production by fermentation", App Microbiol Biotechnol, 78:379-89 (2008).
English Summary of Office Action IL 248989 (with Third Party Submission) dated Sep. 6, 2017.
English Translation of Defendant-Intervenor brief in Appeal No. 2019Heo3618, KR (Korea) 1787310, dated Oct. 23, 2019.
English Translation of KIPO Response Correction in Appeal No. 2019Heo3618, KR (Korea) 1787310, dated Oct. 22, 2019.
English Translation of KIPO Response in Appeal No. 2019Heo3618, KR (Korea) 1787310 dated Oct. 15, 2019.
English Translation of Packaging in Mintel Database, Record ID 743114, Catzy Hair Colourant, Published Jul. 2007. Translation Filed Feb. 2, 2018.
Evans, "Fatigue testing of hair—A statistical approach to hair breakage", J Cosmet. Sci., 60:599-616 (2009).
Evans, et al., "A statistical analysis of hair breakage. II. Repeated grooming experiments", J. Cosmet. Sci., 61:440-455 (2010).
EX 1048, PGR 2018-00025, Public version of Ex 1036, Laboratory Notebook, filed Oct. 10, 2018.
EX 1063, Signori, International Journal of Cosmetic Science, (1997).
EX 1065, Practical Modern Hair, Science, Chapter 4, (2012).
EX 2003—Liqwd v. L'Oreal 2018 WL480759 (Fed.Cir 2018).
EX 2004—Trial Testimony in Liqwd, Inc. et al. v. L'Oreal (UK) Ltd. et al., EQHC Patents Court, Claim No. HP-2016-000056, Apr. 26, 2018.
EX 2010, pGR 2018-00023, Joico Bleach Powder label with instructions and ingredients, filed May 21, 2018.

(56) References Cited

OTHER PUBLICATIONS

Ex 2011, PGR 2018-00023, Clairol Professional Basic White Powder Lightener label with instructions and ingredients filed May 21, 2018.
EX 2024, PGR 2018-00023, Matrix Light Master Bleach Powder label and instructions, filed May 21, 2018.
EX 2025, PGR 2018-00023, Redken Flash Lift Lightening Power label and instructions, filed May 21, 2018.
EX 2026, PGR 2018-00023, Redken Up to 7 Bleach Powder, label and instructions, filed May 21, 2018.
EX 2027, PGR 2018-00023, L'Oreal Quick Blue Bleach Powder label and instructions, filed May 21, 2018.
EX 2034—Felthouse et al., "Maleic Anhydride, Maleic Acid, and Fumaric Acid"—Kirk-Othmer Encyclopedia of Chemical Technology (First Published Oct. 18, 2001).
EX 2036—Maleic Acid Safety Datasheet Vertellus 2011.
EX 2043—Excerpt From Youtube Video Entitled "How Does Smartbond Technology Work?" by L'Oreal Professionnel, Available at https://youtu.be/lmyb5fiellg?t=31 (Visited Oct. 18, 2018).
EX 2044—Redken PH-Bonder Technical Guide—Aug. 2016.
EX 2045, PGR 2018-00025, Matrix Bond Ultim8 Techniques Guide, filed Nov. 16, 2018.
EX 2047, PGR 2018-00025, Matrix Bond Ultim8 bottle instructions, filed Nov. 16, 2018.
EX 2048, pGR 2018-00025, Matrix Bond Ultim8 package instructions, filed Nov. 16, 2018.
EX 2049, PGR 2018-00025, Lab report from Analyze Inc., filed Nov. 16, 2018.
EX 2050, PGR 2018-00025, Redken pH Bonder bottle instructions, filed Nov. 16, 2018.
EX 2051, PGR 2018-00025, Redken pH Bonder package instructions, filed Nov. 16, 2018.
EX 2052, PGR 2018-00025, L'Oreal Professional Smartbond bottle instructions, filed Nov. 16, 2018.
EX 2053, PGR 2018-00025, L'Oreal Professional Smartbond package instructions, filed Nov. 16, 2018.
EX 2055—Wolfram, "The Reactivity of Human Hair. A Review" Hair Research, 1981.
EX 2056—Dubief et al., Chpt 4 "Hair Care Products" From the Science of Hair Care (Bouillon C, Wilkinson, J. Eds.), 2D Edn. 2005.
EX 2058—Types of Professional Haircolor Services (Redken), https:www.redken.com/haircolor/types-of-professional-haircolor-services (Obtained Jun. 2, 2018).
EX 2060—Corbett, "The Chemistry of Hair-Care Products" J. Soc'y of Dyers and Colourists 92(8):285-303, 1976.
EX 2063—Harris, Chpt 9, "Monoprotic Acid-Base Equilibira" From the Science of Hair Care (Bouillon C, Wilkinson j, Eds., 2D Edn., 2005.
EX 2066—Harris, Chpt 10, "Polyprotic Acid-Base Equilibria" From Quantitative Chemical Analysis, 7th Ed., 2007.
EX 2073—(PGR 2018-00025)—Redacted Declaration of Dean Christal, dated Oct. 31, 2018.
EX 2074—(PGR 2018-00025)—Redacted Declaration of Edward T. Borish, PhD dated Nov. 16, 2018.
EX 2075, PGR 2018-00025, Redacted LIQWD Inc. Patent Owner Response under 37 CFR 42.220, dated Nov. 16, 2018.
Examination Report GB1513932.2 dated Sep. 26, 2016.
Examination Report GB1605346.4 dated Jan. 11, 2017.
Expert Village, Hair color mixing and aopplication techniques: Mixing bleach for highlights, https://www.youtube.com/watch?v=nOE_BaC57mw, 3 pages, retrieved from the internet May 17, 2016.
Facebook page, https://www.facebook.com/behindthechair/photos/a.153398501906.116563.44389181906/10152417864161907/?type=3&theater, May 13, 2014.
Facebook page, https://www.facebook.com/GuyTangHairArtist/photos/a.254923251198058.69129.214382105252173/762062380484140/?type=3&theater, Apr. 17, 2014a.
Facebook page, https://www.facebook.com/GuyTangHairArtist/photos/a.254923251198058.69129.214382105252173/762551773768534/?type=3&theater, Apr. 17, 2014b.
Facebook page, https://www.facebook.com/GuyTangHairArtist/photos/a.254923251198058.69129.214382105252173/767530266604018/?type=3&theater, Apr. 26, 2014.
Facebook page, https://www.facebook.com/GuyTangHairArtist/photos/a.254923251198058.69129.214382105252173/772484942775217/?type=3&theater, May 7, 2014.
Facebook page, https://www.facebook.com/olaplex/photos/a.541423639298984.1073741828.347578558683494/574713415970006/?type=3&theater, Apr. 11, 2014.
Facebook page, https://www.facebook.com/traceycunninghamcolor/posts/10202245158143314, Mar. 9, 2014.
Facebook page, https://www.facebook.com/olaplex/573114059463275, Apr. 7, 2014.
Facebook page, https://www.facebook.com/traceycunninghamcolor/posts/10152466366701095, May 11, 2014.
Fed Cir. decision in Appeal No. 2018-2152, Oct. 17, 2019.
Fibreplex No. 1 Bond Booster, Icare, accessed Oct. 11, 2017.
Fibreplex No. 1 Label, 6 pages, accessed Feb. 28, 2018.
Fibreplex Safety Date Sheet, 5 pages, issued Mar. 16, 2016.
FMC Webinar—The Science of Persulfate Activation, Apr. 24, 2013.
Fueghelman, et al., "Morphology and Properties of Hair", Hair and Hair Care: Cosmetic Science and Technology Series, 17(1): 1-15 (1997).
Gamez-Garcia, et al., "Patterns of Light Interference", Journal of Cosmetic Science, 58(4): 269-282 (2007).
Gamez-Garcia, et al., "Understanding Properties of Hair Cuticle", Journal of Cosmetic Science, 423-424 (2006).
Gobbo, et al., "Improved Methodology for the Preparation of Water-Soluble, Malemide-Functionalized Small Gold Nanoparticles", Langmuir, ACS Publications, 28:12357-12363 (2012).
Grounds of Invalidity filed by L'Oreal (UK) Limited, et al., on Nov. 4, 2016.
Guy Tang on Instagram page, https://www.instagram.com/p/nPmHn7mnA6/ Apr. 26, 2014.
Haake, et al., "Hair breakage—How to measure and counteract", J. Cosmet. Sci., 60:143-151 (2009).
Haddleton CV Jan. 2, 2018.
Haddleton report dated Feb. 2, 2018 (REDACTED).
Haddleton report dated Mar. 29, 2018 (REDACTED).
Haddleton report, dated Apr. 24, 2018.
Halal "The Chemistry of Haircolor," Slide 36, http://chemistrysimplified.com/wp-content/uploads/2015/07/CEA-2015-Chemistry-of-Haircolor.pdf (2015).
Halal, Hair Structure and Chemistry Simplified, 322 pages (2009).
Hall and Wolfram, "Application of the theory of hydrophobic bonds to hair treatments," J Soc Cosmet Chem., 28:231-41 (1977).
Hefferd Declaration Part 1 of 3—REDACTED—filed in *Liqwd, Inc. et al.* v. *L'Oreal USA, Inc. et. al.*, U.S. District Court for the District of Delaware, Civil Action No. 1:17-cv-00014—Apr. 17, 2017.
Hefferd Declaration Part 2 of 3—REDACTED—filed in *Liqwd, Inc. et al.* v. *L'Oreal USA, Inc. et. al.*, U.S. District Court for the District of Delaware, Civil Action No. 1:17-cv-00014—Apr. 17, 2017.
Hefferd Declaration Part 3 of 3—REDACTED—filed in *Liqwd, Inc. et al.* v. *L'Oreal USA, Inc. et. al.*, U.S. District Court for the District of Delaware, Civil Action No. 1:17-cv-00014—Apr. 17, 2017.
Hefford, Robert—report, dated Apr. 25, 2018.
Hefford, Robert—report, dated Feb. 2, 2018.
Hefford, Robert—report, dated Mar. 29, 2018.
Hierarchical Structure, https://www.upload.wikimedia.org/wikipedoa/commons/thumb/5/55/Hierarchical_structure, retrieved from the internet Sep. 22, 2016.
HiMedia Labs, http://www.himedialabs.com/TD/AT068.pdf, downloaded on Mar. 6, 2018, pp. 1-2, 2011.
Hoshowski, "Conditioning of Hair", Hair and HairCare, 17(4):65-104 (1997).
Hoyle, et al., "Thiol-click chemistry: a multifaceted toolbox for small molecule and polymer synthesis", Chemical Society Reviews, 39:1355-1387 (2010).

(56) References Cited

OTHER PUBLICATIONS

INCI listing ingredient BIS Aminopropyl Diglycol Dimaleate Cosmetics Cosing EC Regulation v2, Mar. 29, 2018.
Institution of Cancellation Proceeding for KR (Republic of Korea) 10-2016-7034158, dated May 17, 2018, with English Translation.
International Search Report and Written Opinion for PCT/US2015/031166 dated Jan. 22, 2016.
International Search Report and Written Opinion for PCT application, PCT/US2015/065032, dated May 9, 2016.
International Search Report and Written Opinion for PCT/US2014/049388 dated Oct. 29, 2014.
International Search Report and Written Opinion for PCT/US2016/029215 dated Jul. 8, 2016.
International Search Report and Written Opinion for PCT/US2016/058432, dated Jan. 16, 2017.
Isaacman, "Just Click It: New Chemical Reactions for Cosmetic Applications", Cosmetics & Toiletries, https://www.cosmeticsandtoiletries.com/research/techtransfer/premium-Just-Click-It-New-Chemical-Reactions-for-Cosmetic-Applications-209714931.html, accessed Apr. 5, 2018.
Jachowicz, "Hair damage and attempts to its repair". J Soc Cosmet Chem., 38:263-86 (1987).
Jankowksa, et al., "The Relations Between Ionic and Non-Ionic Diffusion of Sulfonamides Across the Rabbit Cornea", Investigative Ophthalmology & Visual Science, 27(1):29-37 (1986).
Japanese Office Action for JP 2016-515948 dated Jan. 25, 2017 (with English Translation).
Japanese Office Action for JP 2016-515948 dated Jul. 29, 2016 (with English Translation).
John Corbett, Hair Colorants: Chemistry and Toxicology 1-54 (1998).
JOICO VeroLight Dust-Free Lightening Powder Sleek Shop accessed Mar. 28, 2018.
JP 2016572832 Pre-Appeal Examination report, Mar. 28, 2019 in English.
Kade, et al., "The Power of Thiol-ene Chemistry", J. Polymer Science Part A: Polym. Chem., 48:743-750 (2010).
Kamath and Robbins, "Hair breakage by combing and brushing—A comment on: T.A. Evans and K. Park, A statistical analysis of hair breakage. II Repeated grooming experiments", J. Cosmet. Sci., 41:439-56 (2010).
Kang, "Hair Dyeing and Hair Damage According to the Number of Dyeing", Master's Thesis, Kwangju Women's University, 11-13 (2006) with English Translation.
Keshouhin kagaku guide [Cosmetic Science Guide] 2nd edition, Fragrance Journal Ltd.,May 16, 2011,p. 256-257 with English description.
KIPO Response Correction in Appeal No. 2019Heo3618, KR (Korea) 1787310 dated Oct. 22, 2019.
KIPO Response in Appeal No. 2019Heo3618, KR (Korea) 1787310 dated Oct. 15, 2019.
Kirschenbaum, et al., "Oxygen radicals from photoirradiated human hair: An ESR and fluorescence study", J Cosmetic Sci., 51:169-182 (2000).
Kline, htt://homepage.smc.edu/kline_peggy/Organic/Amino_Acid_pKa.pdf, obtained online on Mar. 6, 2019, p. 1 (2006).
Kolb, et al., "Click Chemistry: Diverse Chemical Function from a Few Good Reactions", Agnew. Chem. Int. Ed., 40:2004-2021 (2001).
Koval, "Reactions of Thiols," Russian J Organic Chemistry, 43(3):319-49 (2007).
KR 10-1787310 Decision on Cancellation dated Mar. 5, 2019 with Eng Translation.
KR 20030003970—Certified English Tranlsation Jan. 14, 2003 LG Household & Health Care, Ltd.
KR Decision on Cancellation, dated Mar. 5, 2019 with Eng Translation.
L'Oreal Invalidity Opinion Ex A01, filed Jul. 26, 2018.
L'Oreal Invalidity Opinion Ex A02, filed Jul. 26, 2018.
L'Oreal Invalidity Opinion Ex A03, filed Jul. 26, 2018.
L'Oreal Invalidity Opinion Ex A04, filed Jul. 26, 2018.
L'Oreal Invalidity Opinion Ex A05, filed Jul. 26, 2018.
L'Oreal Invalidity Opinion Ex A06, filed Jul. 26, 2018.
L'Oreal Invalidity Opinion Ex A07, filed Jul. 26, 2018.
L'Oreal Invalidity Opinion Ex A08, filed Jul. 26, 2018.
L'Oreal Invalidity Opinion Ex A09, filed Jul. 26, 2018.
L'Oreal Invalidity Opinion Ex A10, filed Jul. 26, 2018.
L'Oreal Invalidity Opinion Ex A11, filed Jul. 26, 2018.
L'Oreal Invalidity Opinion Ex A12, filed Jul. 26, 2018.
L'Oreal Invalidity Opinion Ex A13, filed Jul. 26, 2018.
L'Oreal Invalidity Opinion Ex A14, filed Jul. 26, 2018.
L'Oreal Invalidity Opinion Ex A15, filed Jul. 26, 2018.
L'Oreal Invalidity Opinion Ex A16, filed Jul. 26, 2018.
L'Oreal Invalidity Opinion Ex A17, filed Jul. 26, 2018.
L'Oreal Invalidity Opinion Ex A18, filed Jul. 26, 2018.
L'Oreal Invalidity Opinion Ex A19, filed Jul. 26, 2018.
L'Oreal Invalidity Opinion Ex A20, filed Jul. 26, 2018.
L'Oreal Invalidity Opinion Ex A21, filed Jul. 26, 2018.
L'Oreal Invalidity Opinion Ex A22,filed Jul. 26, 2018.
L'Oreal Invalidity Opinion Ex A23, filed Jul. 26, 2018.
L'Oreal Invalidity Opinion Ex A24, filed Jul. 26, 2018.
L'Oreal Invalidity Opinion Ex A25, filed Jul. 26, 2018.
L'Oreal Invalidity Opinion Ex A26, filed Jul. 26, 2018.
L'Oreal Invalidity Opinion Ex A27, filed Jul. 26, 2018.
L'Oreal Invalidity Opinion Ex A28, filed Jul. 26, 2018.
L'Oreal Invalidity Opinion Ex A29, filed Jul. 26, 2018.
L'Oreal Invalidity Opinion Ex A30, filed Jul. 26, 2018.
L'Oreal Invalidity Opinion Ex A31, filed Jul. 26, 2018.
L'Oreal Invalidity Opinion Ex A32, filed Jul. 26, 2018.
L'Oreal Invalidity Opinion Ex A33, filed Jul. 26, 2018.
L'Oreal Invalidity Opinion Ex A34, filed Jul. 26, 2018.
L'Oreal Invalidity Opinion Ex A35, filed Jul. 26, 2018.
L'Oreal Invalidity Opinion Ex A36, filed Jul. 26, 2018.
L'Oreal Invalidity Opinion Ex A37, filed Jul. 26, 2018.
L'Oreal Invalidity Opinion Ex A38, filed Jul. 26, 2018.
L'Oreal Invalidity Opinion Ex A39, filed Jul. 26, 2018.
L'Oreal Invalidity Opinion Ex A40, filed Jul. 26, 2018.
L'Oreal Invalidity Opinion Ex A41, filed Jul. 26, 2018.
L'Oreal Invalidity Opinion Ex A42, filed Jul. 26, 2018.
L'Oreal Invalidity Opinion Ex A43, filed Jul. 26, 2018.
L'Oreal Invalidity Opinion Ex A44, filed Jul. 26, 2018.
L'Oreal Invalidity Opinion Ex A45, filed Jul. 26, 2018.
L'Oreal Invalidity Opinion Ex A46, filed Jul. 26, 2018.
L'Oreal Invalidity Opinion Ex A47, filed Jul. 26, 2018.
Lab muffin "How Does Olaplex Hair Treatment Work?" http://www.labmuffin.com/2015/04/how-does-hair-treatment-work, 8 pages retrieved from the internet Jun. 24, 2016.
Law, Robert—Declaration dated Jul. 13, 2018, Filed by L'Oreal in GB 1605346.4 and GB 1813313.2.
LEWIS excerpt from Hawley's Condensed Chemical Dictionary, 5 pages (1997).
*Liqwd* vs. *L'Oreal (UK) Ltd.*, Amended Invalidity Grounds Nov. 6, 2017.
Majonis, et al., "Dual-purpose polymer labels for fluorescent and mass cytometric affinity bioassays," Biomacromolecules, 14(5):1503-13 (2013).
Mayo, et al., "Effect of Spacer Chemistry on the Formation and Properties of Linear Reversible Polymers", Journal of Polymer Chemistry, Part A: Polymer Chemistry, 51:5056-5066 (2013).
Memorandum filed in response to official action dated Jun. 5, 2017 in corresponding Israel application No. 248989.
Memorandum Order in *Liqwd, Inc. et al.* v. *L'Oréal USA, Inc. et al.*, Case No. 1:17-cv-00014 (D. Del), denying Motion for Preliminary Injunction by Judge Sue L. Robinson (Jul. 6, 2017).
Mhaskar, et al., "Hair breakage index: An alternative tool for damage assessment of human hair", J. Cosmet. Sci., 62:203-207 (2011).
Mintel Database Record ID 1999129, L'Oreal Preference Les Blondissimes Hair Colourant, 2013.
Mintel Database, Record ID 743214, Catzy Hair Colourant, 4 pages, Published Jul. 2007.
Mintel Leave-in Hair and Scalp Nutrient, XP002743522, Database accession No. 10141004, Jun. 1, 2003.

(56) References Cited

OTHER PUBLICATIONS

Mintel Permanent Hair Colour, XP002743523, Database Accession No. 2061070, May 1, 2013.
Morgan, et al., "Interaction of Maleic Acid with Thiol Compounds", Biochemical Laboratory, Cambridge, 733-742 (1983).
MSDS Olaplex No. 1 Bond Multiplier, dated Jun. 2014.
MSDS Olaplex No. 2 Bond Perfector, updated Jul. 2014.
Murota, et al. J Investig Allergol Clin Immunol, 18(4):245-252, (2008).
Nair, et al., "The Thiol-Michael Addition Click Reaction: A Powerful and Widely Used Tool in Materials Chemistry", Chemistry of Materials, 26:724-744 (2014).
Nandagiri, Arun—Declaration signed Jan. 30, 2017 (Ex. 1008) with CV (Ex. 1016).
Nandagiri, Arun—Deposition transcript dated Mar. 2, 2018 (Ex 2055).
Nandagiri, Arun—Deposition transcript dated Mar. 14, 2018 (Ex 2057).
Nandagiri, Arun—Deposition transcript dated Oct. 6, 2017.
Nandagiri, Arun—Rebuttal Declaration dated Jan. 26, 2018 (Ex 1040).
Nandagiri, Arun—Rebuttal Declaration, pp. 1-7, Jan. 30, 2017.
Naver Encyclopedia, Trichology Dictionary: Developer, with English Translation (2003).
New Olaplex Usage Instructions label (Jun. 2014).
Notification of Grant for GB 1513932.2 dated Oct. 4, 2016.
Office Action ARIPO AP/P/2015/008934, dated May 27, 2019.
Office Action AU (Australia) 2017251818, dated May 31, 2019.
Office Action BR (Brazil) 1120160022556, dated Aug. 6, 2019, with English Summary.
Office Action BR (Brazil) 112016026378-2, dated Aug. 14, 2019, with English Summary.
Office Action CA (Canada) 2947303, dated Jul. 12, 2019.
Office Action CN (China) 201580026039, dated Jul. 16, 2019 with English Summary.
Office Action CU (Cuba) 2016-0017 dated Jul. 3, 2018 (with English Translation).
Office Action EA (Eurasia) 201592291, dated Jul. 9, 2019, with English Translation.
Office Action EA (Eurasia) 201692315, with English Translation, dated Oct. 23, 2019.
Office Action EP (Europe) 17163334, dated Jun. 18, 2019.
Office Action for AU 2015258904 dated Nov. 2, 2016 (Examination Report).
Office Action for AU 2015258904 dated Oct. 26, 2017.
Office Action for CA (Canada) 2,947,303 dated Sep. 8, 2017.
Office Action for CA (Canada) 2,947,303 dated Dec. 28, 2016.
Office Action for CA (Canada) 2,947,303 dated Mar. 19, 2019.
Office Action for CA (Canada) 2,947,303 dated May 12, 2017.
Office Action for CA (Canada) 2947303—dated Sep. 17, 2018.
Office Action for CA (Canada) 2947303, dated Oct. 10, 2018.
Office Action for CA (Canada) CA 2,947,303 dated Dec. 21, 2017.
Office Action for CL (Chile) 201600158 dated Jun. 18, 2018, with English Summary.
Office Action for CL (Chile) 201602911—dated Sep. 27, 2018, with English Summary.
Office Action for CL (Chile) 201602911 dated Apr. 11, 2018, with English Translation.
Office Action for CN (China) 201480042200.1 dated Jan. 1, 2018.
Office Action for CN (China) 201480042200.1 dated May 2, 2017 (with English summary).
Office Action for CN (China) 201480042200.1 with English summary, dated Apr. 22, 2019.
Office Action for CN (China) 201480042200.10 dated Aug. 3, 2018 with English Summary.
Office Action for CN (China) 201480042200.10, dated Nov. 9, 2018, with English Summary.
Office Action for CN (China) 201580026038.9—dated Sep. 5, 2018 with English Summary.
Office Action for CN (China) 201580026038.9 with English summary, dated Apr. 11, 2019.
Office Action for CN (China) 201580026038.90 dated Dec. 18, 2017, with English Summary.
Office Action for CO (Colombia) 16-030.965 dated Jul. 28, 2017 (with English summary).
Office Action for CU (Cuba) 2016-0017 dated Jan. 26, 2018.
Office Action for CU (Cuban) 2016-0017 dated Jun. 20, 2018 (English Translation).
Office Action for DO (Dominican Republic) P20160030 dated Apr. 10, 2018 (English Summary).
Office Action for DO (Dominican Republic) P20160030, dated Sep. 18, 2018, with English Summary.
Office Action for EA (Eurasia) 201592291 dated May 8, 2018, with English Translation.
Office Action for EA (Eurasia) 201592291, dated Aug. 30, 2018, with English Summary.
Office Action for EA (Eurasia) 2016-92315 dated Jan. 30, 2019 with English Summary.
Office Action for EA (Eurasia) 201692315 dated May 17, 2018, with English Translation.
Office Action for EA (Eurasia) 201692315 dated with English translation, dated Sep. 28, 2017.
Office Action for EA (Eurasia)201592291 dated Aug. 1, 2017.
Office Action for EG (Egypt) 2016111820, dated Nov. 26, 2018, with English Translation.
Office Action for EP (Europe) 15725209.9 dated May 16, 2019.
Office Action for EP (Europe) 15725209.9 dated Jan. 1, 2018.
Office Action for EP (Europe) 16798857.5 dated Feb. 19, 2019.
Office Action for EP (Europe) 17163334.0 dated Apr. 26, 2018.
Office Action for EP (Europe) 15725209.9, dated May 18, 2017.
Office Action for EP 15725209.9, dated Aug. 15, 2018.
Office Action for GB (United Kingdom) 1813313.2, dated Sep. 20, 2018.
Office Action for GB (United Kingdom) 1605344.9 dated Apr. 29, 2016.
Office Action for GE (Georgia) AP 2014 01404 dated May 4, 2017 (with English translation).
Office Action for HN (Honduras) 2016-000236 dated Feb. 1, 2019 with English Translation.
Office Action for ID P00201600646, dated Jan. 21, 2019 with English Translation.
Office Action for IL (Israel) 248989, dated Oct. 7, 2018 with English Summary.
Office Action for IL (Israel) 248989 dated Mar. 4, 2018.
Office Action for IL (Israel) 248989 with Third Party Observation dated Sep. 6, 2017 (English Summary).
Office Action for IL (Israel) 248989, dated Jun. 5, 2017 (with English summary).
Office Action for IN (India) 20147007019.00, dated Sep. 6, 2018, with English Translation.
Office Action for IN (India) 201617038524, dated May 12, 2018, with English Translation.
Office Action for JP (Japan) 2016-572832, dated Oct. 26, 2017 (English Translation).
Office Action for JP (Japan) 2016-515948, dated Oct. 3, 2017.
Office Action for JP (Japan) 2016-515948, dated Jun. 27, 2017.
Office Action for JP (Japan) 2016-572832 dated Jun. 2, 2017 (with English summary).
Office Action for JP (Japan) 2016-572832 with English summary, dated Dec. 11, 2018.
Office Action for JP (Japan) 2016-572832, dated Aug. 2, 2018, with English Translation.
Office Action for JP (Japan) 2016-572832, dated Jul. 31, 2018, English Translation.
Office Action for JP (Japan) 2016515948, dated Jun. 27, 2017, English Tranlsation.
Office Action for JP (Japan) 2017-152453 dated May 14, 2019, English summary.
Office Action for JP (Japan) 2017-152453 with English summary, dated Oct. 30, 2018.
Office Action for KR (Republic of Korea) 10-2016-7034158, dated Apr. 10, 2017 (with English summary).

(56) References Cited

OTHER PUBLICATIONS

Office Action for MX (Mexico) MX/a/2016/014917, dated Dec. 7, 2018, with English Summary.
Office Action for MX (Mexico) MX/a/2016/014917, dated Jun. 20, 2018.
Office Action for MX (Mexico) MXa/2016/00176 dated Aug. 24, 2017.
Office Action for NZ (New Zealand) 725652 dated Apr. 3, 2017 (Examination Report).
Office Action for NZ (New Zealand) 725652 dated Oct. 13, 2017 (Examination Report).
Office Action for NZ (New Zealand) 725652, dated May 22, 2018 (Examination Report).
Office Action for PA (Panama) 91418-01 dated Jun. 8, 2017 (with English summary).
Office Action for PA (Panama) dated Jan. 31, 2017 (with English summary).
Office Action for SA (Saudi Arabia) 516370509, dated May 25, 2017 (with English summary) (Examination Report).
Office Action for SA (Saudi Arabia) 516370509, received Aug. 1, 2017 with English Summary.
Office Action for SG (Singapore) 11201609005Q, dated May 24, 2017.
Office Action for SG (Singapore) 11201609005Q, dated Nov. 29, 2017.
Office Action for SG (Singapore) 11201609005Q, dated Sep. 28, 2018.
Office Action for SV (El Salvador) 20160019660, dated Mar. 14, 2018, with English Translation.
Office Action for SV (El Salvador) 2016005320, dated Oct. 5, 2018.
Office Action for UA (Ukraine) a201601137 dated Jun. 22, 2017 (with English translation).
Office Action for UK (United Kingdom) 1618547.2 dated Nov. 30, 2016.
Office Action for U.S. Appl. No. 14/713,885, dated Aug. 17, 2015.
Office Action for U.S. Appl. No. 15/087,415, dated May 23, 2016.
Office Action for U.S. Appl. No. 15/290,593 dated Jan. 2, 2018.
Office Action for U.S. Appl. No. 15/290,593, dated Aug. 1, 2018.
Office Action for U.S. Appl. No. 15/415,464 dated Mar. 15, 2017.
Office Action for U.S. Appl. No. 15/626,453 dated May 14, 2019.
Office Action for U.S. Appl. No. 15/854,504, dated Mar. 7, 2019.
Office Action for U.S. Appl. No. 15/855,719, dated Mar. 25, 2019.
Office Action for U.S. Appl. No. 15/940,150, dated May 16, 2018.
Office Action for U.S. Appl. No. 15/955,455, dated Jun. 26, 2018.
Office Action ID (Indonesia) P00201600646, dated May 25, 2018, with English Translation.
Office Action IN (India) 201647007019, dated Aug. 2, 2019 with English Translation.
Office Action MX (Mexico) MX/a/2016/014917, dated Apr. 12, 2019 with English Summary.
Office Action MY (Malaysia) PI 2016700195 dated Sep. 30, 2019.
Office Action SV (El Salvador) Application No. 2016-0019660 dated Mar. 18, 2019 with English Summary.
Office Action U.S. Appl. No. 15/854,504 dated Aug. 8, 2019.
Official communication in GB 1513932.2 (dated Apr. 13, 2016).
Official communication in UK Patent Application 1513932.2 (dated Apr. 13, 2016).
Ogata and Sawaki, et al., "Kinetics of the Acid-Catalysed Formation of Aliphatic Peracids from Hydrogen Peroxide and Aliphatic Acids in Dioxin" Tetrahedron, 21:3381-3386, (1965).
Olaplex "The Olaplex Difference" https://olaplex.com/pages/how-it-works, retrieved from the internet Dec. 12, 2017.
Olaplex Bond Multiplier No. 1 Mix with Highlights, balayage, or high lift color label (Jun. 2014).
Olaplex on Instagram page, https://www.instagram.com/p/mGhswioJQ2/?hl=en, Mar. 28, 2014.
Olaplex on Instagram page, https://www.instagram.com/p/mvxsbUoJSI/?hl=en, Apr. 13, 2014.
Olaplex on Instragram page, https://www.instagram.com/p/nBwLbtoJck/?hl=en, Apr. 20, 2014.

Olaplex, Apparent description of booth presentation during Bronner Bros, show in Atlanta http://www.instagram.com/p/zacpQulJfn/, Instagram post Feb. 22, 2015.
Olaplex, Material Safety Data Sheet for Olaplex Bond Multiplier No. a Dec. 2014.
Olaplex.com, "Never break a client's hair", visited Jun. 28, 2014.
Partial International Search Report for PCT application, PCT/US2015/065032, dated May 9, 2016.
Partial International Search Report for PCT/US2015/031166 dated Sep. 14, 2015.
Paterson, et al., "On the synthesis of N-maleoyl amino acids in aqueous media: cautionary tales for the unwary traveller", ARKAT USA, Inc., 11-16 (2010).
PGR 2017-00011 Decision denying Institution of Post-Grant Review, by Patent Trial and Appeal Board, Paper 24 (dated Jul. 19, 2017).
PGR 2017-00012 Petition for Post-Grant Review of U.S. Pat. No. 9,498,419, filed on behalf of L'Oreal USA, Inc. (Jan. 31, 2017).
PGR 2017-00012—REDACTED version of Paper 102, Final Written Decision, dated Jun. 27, 2018 (Paper 105).
PGR 2017-00012 Decision partial Institution of Post-Grant Review, by Patent Trial and Appeal Board, Paper 17 (dated Jul. 19, 2017).
PGR 2017-00012 Liqwd, Inc.'s Patent Owner Response under 37 C.F.R. §42.220, filed on Oct. 20, 2017 (REDACTED).
PGR 2017-00012 Patent Owner's First Amended Rule 30(b)(6) Deposition Notice, dated May 2, 2017.
PGR 2017-00012 Patent Owner's Supplemental Response, Novelty, dated May 24, 2018.
PGR 2017-00012 Petitioner's REPLY to Patent Owner's Supplemental Response dated May 31, 2018.
PGR 2017-00012 Redacted Petitioners reply to patent owner's response, pp. 1-32 dated Jan. 2, 2018.
PGR 2018-00023 Paper 9 Institution Denied, dated Aug. 10, 2018.
PGR 2018-00023 Patent owner's preliminary response, pp. 1-76, dated May 21, 2018.
PGR 2018-00024—Wickett, Randall Declaration.
PGR 2018-00024 Patent owner's preliminary response, pp. 1-76, dated May 21, 2018.
PGR 2018-00025—Wickett, Randall Declaration.
PGR 2018-00025 Patent owner's preliminary response, pp. 1-51, dated May 21, 2018.
PGR 2018-00025; EX 1062; Wickett Reply Declaration, Redacted, dated Feb. 15, 2019.
Plaintiff's Opening Brief in Support of Motion for Preliminary Injunction, redacted—public version, filed Jan. 18, 2017.
PO and Senozan article re: Henderson-Hasselbalch Equation, 2001 (Exhibit 2052).
Pomogailo, et al., "Monomeric and Polymeric Carboxylic Acids", Springer Series in Materials Science, 138(2):7-25 (2010).
Pramanik, "10.3.7 DS—Salt Interaction", Characterization of Impurities and Degradants Using Mass Spectrometry, John Wiley & Sons, Hoboken, New Jersey, (2011).
Pressly, Eric D.—Declaration, signed Oct. 19, 2017 (REDACTED) filed in PGR 2017-00012.
Public Version of Final Written Decision, dated Jul. 30, 2019.
Quantitative Chemical Analysis, pp. 1027-1 thru 1027-5, Daniel Harris Editor, 3rd Ed., (1991).
Ramachandra, et al., "Acid-based characteristics of human hair: Absorption of HCl and NaOH, and the effects on physical properties." J Soc Comet Chem., 32:393-405 (1981).
Randebrock, "Neue Erkenntnisse Uber den morphologischen aufbau des menschlichen haares," J Soc Cos. Chem., 15:691-706 (1964).
Redacted Version of Declaration of Robert J.W. Hefford, PhD with Appendices (1-3) and Exhibits (A-O), filed in *Liqwd, Inc et al.* v. *L'Oréal USA, Inc. et al.*, U.S. District Court for the District of Delaware, Civil Action No. 1:17-cv-00014 on Apr. 17, 2017.
Refinery, "Fire Your Colorist if They Are Not Using This" http://www.refinery20.com/olaplex-hair-color, 6 pages, retrieved from the internet Jun. 24, 2016.
Relaxing agents, Milday Standard Cosmetology, pp. 618-625, 13th edition, (2016).
Robbins and Crawford, et al., "Cuticle Damage and the Tensile Properties of Human Hair", J. Soc. Cosmet. Chem., 42:59-67 (1991).

(56) References Cited

OTHER PUBLICATIONS

Robbins, Chapter 10, Chemical and Physical Behavior of Human Hair, 5th Edition, 2012.
Robbins, Chapter 4 "Bleaching Human Hair" in Chemical and Physical Behavior of Human Hair 2002.
Robbins, Chapter 5 "Bleaching and Oxidation of Human Hair" in Chemical and Physical Behavior of Human Hair 2012.
Robbins, Chapter 6 "Interactions of Shampoo and Conditioner Ingredients with Hair" in Chemical and Physical Behavior of Human Hair 2012.
Robbins, Clarence R., Mouhatu no kagaku [Science of Hair], 4th edition,Fragrance,Journal Ltd.,Jul. 10, 2006,p. 221-225 with English counterpart, p. 194-198.
Robbins, et al., "Chemical Composition of Different Hair Types" Chemical and Physical Behavior of Human Hair ,Chapter 2:104-76, Springer-Verlag, Berlin Heidelberg (2012).
Robbins, et al., "Dyeing Human Hair", Chemical and Physical Behavior of Human Hair, Chapter 7, Springer-Verlag, Berlin Heidelberg (2012).
Robbins, et al., "Polymerization into Human Hair", J. Soc. Cosmet. Chem., 25:407-421 (1974).
Robbins, et al., "The Physical Properties of Hair Fibers", Chemical and Physical Behavior of Human Hair, Chapter 9, Springer-Verlag, Berlin Heidelberg (2012).
Robinson, "A study of damaged hair", J. Soc. Cosmet. Chem., 27:155-161 (1976).
Ruetsch, et al., "Photodegradation of human air: An SEM study", J. Cosmet. Sci., 51:103-125 (2000).
Sandhu, et al., "A simple and sensitive method using protein loss measurements to evaluate damage to human hair during combing", J. Soc. Cosmet. Chem., 46:39-52 (1995).
Second Written Opinion for corresponding Singapore Application No. 11201609005Q dated Nov. 29, 2017.
Shansky, "Toning of Human Hair with Fiber Reactive Dyestuffs," Cosmetics and Toiletries, 91(11):46-48 (1976).
Shansky, "The Reaction Mechanism of Fiber Reactive Dye stuffs with Hair Keratin," American Perfumer and Cosmetics (1966).
Sigma-Aldrich website BM PEG 3 1 11 Bismaleimido Triethyleneglycol (2018).
Slavin, et al. "Biological surface modification by 'thiol-ene' addition of polymers synthesized by catalytic chain transfer polymerization (CCTP)," Polymer Chem., 3:1461-6 (2012).
Slavin, et al., "Biological surface modification by thiol-enel addition of polymers synthesized by catalytic chain transfer polymerization (CCTP)", Polymer Chem., 3:1461-6 (2012).
Statement—Amended Reply Statement of Case on Validity (KR970, WO768 and Catzy), dated Nov. 28, 2017.
Statement—Reply Statement of Case on Validity (Olaplex), dated Nov. 28, 2017.
Statement of Case on the Term "Simple Salt", dated Jan. 10, 2018.
Statement of Case on Validity (KR970, WO768 and Catzy), dated Nov. 6, 2017.
Success Stories presentation, Oct. 6, 2016.
Swift, Chapter 10, "Mechanical Properties of Hair" in Fundamentals of Human Hair Science, (1997).
Swift, Chapter 11, "Cosmetic Treatments of Hair" in Fundamentals of Human Hair Science, (1997).
Swift, Fundamentals of Human Hair Science, (1997).
Table 2 from Furia, T.E., Sequestrants in Food (Chp. 6) in CRC Handbook of Food Additives (1972).
Table 3.4, pKa values of some amino acids, From: Appendix: Acid-Base Concepts Biochemistry 5th edition. Berg JM, Tymoczko JL, Stryer L.New York: W H Freeman; (2002).
Tate, et al., "Quantification and prevention of hair damage", J. Soc. Cosmet. Chem., 44:347-371 (1993).
The Power Of One http://www.nxtbook.com/nctbooks/creativeage/Launchpad_201405/index.php?srartid, 401 page, retrieved from the internet Jun. 24, 2016.
Thermo Fisher Scientific , "Bismaleimide Cross linkers (BMOE, BMBandBMH)," product instructions, pp. 1-3 (2012).
Thermo Scientific, "Instructions BM (PEG) 2 and BM (PEG) 3" (2012).
Third party observation for GB 1513932.2 (Jan. 2016).
Third Party Observation AU (Australia) 2017251818, dated Jun. 17, 2019.
Third Party Observation for JP (Japan) 2016-572832 with English Translation dated Apr. 19, 2019.
Third Party Observation IL (Israel) 248989 mailed Jan. 10, 2018.
Third Party Observation IN (India) 2016177038524 on Feb. 6, 2019.
Third Party Observation AU (Australia) 2017251818, dated Oct. 2, 2019.
Third Party Observation AU (Australia) 2017251818, filed Jun. 4, 2019.
Third Party Observation AU 2015258904 mailed Dec. 19, 2016.
Third Party Observation BR (Brazil) 1120160263782 Jan. 9, 2018 w/Eng Summary.
Third Party Observation BR (Brazil) 1120160263782 Oct. 23, 2018 w/Eng Summary.
Third Party Observation CA (Canada) 2947303 filed Feb. 19, 2019.
Third Party Observation CA (Canada) 2947303, dated Oct. 25, 2019.
Third Party Observation CA (Canada) 2947303, filed Jun. 12, 2019.
Third Party Observation EA (Eurasia), dated Sep. 13, 2019.
Third Party Observation EP (Europe) 15725209.9 filed Feb. 22, 2019 with Eng Translation.
Third Party Observation EP (Europe) 15725209.9 filed Feb. 22, 2019.
Third Party Observation filed EP14758005.4 (May 13, 2016).
Third Party Observation filed EP14758005.4 (May 18, 2016).
Third Party Observation filed GB1513932.2 (Oct. 3, 2016).
Third Party Observation filed GB1513932.2 (Aug. 23, 2016).
Third Party Observation filed GB1513932.2 (Sep. 22, 2016).
Third Party Observation filed GB1605346.4 (Nov. 11, 2016).
Third Party Observation filed in AU 2017251818, mailed Jan. 17, 2018.
Third Party Observation filed in AU Application No. 2015258904 mailed Oct. 5, 2017.
Third Party Observation filed in EP Application No. 15725209.9 mailed Oct. 27, 2017.
Third Party Observation filed in GB Application No. 1513932.2 (Jan. 2016).
Third Party Observation filed in ID Application No. P00201608726, mailed Mar. 6, 2018.
Third Party Observation filed in JP Application No. 2016-572832 mailed Sep. 29, 2017.
Third Party Observation filed in JP Application No. 2016-572832,mailed May 25, 2018, with English Summary).
Third Party Observation filed in KR (Korea) 101787310 on Jan. 29, 2019.
Third Party Observation filed in MX Application No. MX/a/2016/014917 mailed Nov. 6, 2017.
Third Party Observation filed in NZ Application No. 725652, mailed May 16, 2018—Part 2 of 2.
Third Party Observation filed in NZ Application No. 725652, mailed May 16, 2018—Part 1 of 2.
Third Party Observation filed in U.S. Appl. No. 15/087,415, filed Aug. 29, 2016.
Third Party Observation filed in U.S. Appl. No. 15/087,415, filed Sep. 14, 2016.
Third Party Observation filed in U.S. Appl. No. 15/087,415, filed Aug. 25, 2016.
Third Party Observation filed in U.S. Appl. No. 15/087,415, filed Sep. 23, 2016.
Third Party Observation for (ISRAEL) 248989, mailed Oct. 3, 2018.
Third Party Observation for EA 201692315, filed Nov. 1, 2017, English Translation.
Third Party Observation for EC IEPI 2016-94261, filed Mar. 29, 2017, with English Summary.
Third Party Observation for EP (Europe) 15725209.9 filed May 8, 2019.
Third Party Observation for GB 1605346.4 , dated Oct. 24, 2018.

(56) References Cited

OTHER PUBLICATIONS

Third Party Observation for GB 1605346.4, filed Nov. 30, 2018.
Third Party Observation for GB 1813313.2, dated Jan. 8, 2019.
Third Party Observation GB 1813313.2 filed Apr. 2, 2019.
Third Party Observation GB 1813313.2 filed Mar. 8, 2019.
Third Party Observation GB1513932.2 (Jun. 24, 2016).
Third Party Observation JP (Japan) 2016-572832 filed Sep. 2, 2019 with English summary.
Third Party Observation JP 2016572832 filed Mar. 5, 2019 with Eng Summary.
Third Party Observation KR (Korea) 101787310 on Jan. 29, 2019.
Third Party Observation KR 101787310 filed Jan. 29, 2019 with Eng Translation.
Third Party Observation mailed EP14758005.4 (Dec. 21, 2016).
Third Party Observation mailed EP157250209.9 (Jan. 10, 2017).
Third Party Observation New Zealand NZ 725652 mailed Dec. 19, 2016.
Third Party Observation Submitted GB 1513932.2 (Apr. 20, 2016).
Third Party Observation, EP 15725209.9, mailed Aug. 22, 2018.
Third Party Protest filed in CA 2,947,303, mailed May 8, 2018.
Third Party Protest filed in CA 2,947,303, mailed Dec. 7, 2017.
Third Party Protest for CA 2947303, mailed Feb. 8, 2017.
Third Party Submission for CA 2,947,303, dated Sep. 14, 2018.
Thomas Clausen et al., Hair Preparations, in Ullman's Encyclopedia of Industrial Chemistry (Jul. 15, 2006).
Tracey Cunningham on Instagram page; https://www.instagram.com/p/l_mat6ig-z/, (Mar. 26, 2014).
Tracey Cunningham on Instagram page; https://www.instagram.com/p/l1AF_Zig5e/, (Mar. 22, 2014).
UK High Court Judgement—Jun. 11, 2018—In Relationship to GB 2525793.
Voet, et al., Fundamentals of Biochemistry Excerpt (2008).
Webster's Third International New Dictionary 40 (3rd ed) 2002.
Wenniger, et al., "Maleic Acid", CTFA Cosmetic Ingredient Handbook, 2:226 (1992).
Whewell, "The chemistry of hair" pp. 207-223 A lecture delivered before the Society Dec. 14, 1960.
White and Emmons, et al., "The Chemistry of Permaleic Acid", Tetrahedron, 17:31-34, (1962).
Wicket and Jachowicz, "Measuring Hair", Handbook of Cosmetic Science and Techonology pp. 694-724 Andre Barrel #rd. Ed, (2009).
WPI Accession No. 1995-355152, English abstract of JPH 07242520, Sep. 19, 1995 (retrieved Feb. 2, 2016).
Written Opinion for PCT/US2015/031166, dated Jul. 19, 2016.
Yan, et al., "Cellular association and cargo release of redox-responsive polymer capsules mediated by exofacial thiols," Adv. Mater. 23:3916-3921 (2011).
Yang, et al., "In-Situ Polymerization of Maleic Acid and Itaconic Acid and Crosslinking of Cotton Fabric", Textile Res. J., 69(10):782-789 (1999).
Yang, et al., "Polymerization of Maleic Acid and Itaconic Acid Studied by FT-Raman Spectroscopy", J. Applied Polymer Science, 81:223-228 (2001).
Zhao, et al., "Preparation of peracetic acid from hydrogen peroxide Part I: Kinetics for peracetic acid synthesis and hydrolysis" Journal of Molecular Catalysis A: Chemical, 271:246-252 (2007).
Zumdahl, Chemistry Excerpt, 15:621-622 (1986).
Zviak "The Science of Hair Care," Marcel Dekker, Inc., pp. 263-279(1986).
Zviak & Millequant Chapter 7, "Hair Bleaching" in The Science of Hair Care, (2005) (Exhibit DH 3).
Zviak & Millequant Chapter 9 "Oxidation Colouring", The Science of Hair Care, Informa Healthcare USA, Inc (2008).
Zviak, et al., "Hair Structure, Function, and Physicochemical Properties", The Science of Hair Care, Chapter 1, 1-48 (1986).
Declaration by Dr. Hefford dated Jan. 7, 2020 filed in KR Appeal No. 2019Heo3618.
Declaration by Prof. Steve Rannard dated Dec. 25, 2019 filed in KR Appeal No. 2019Heo3618.
Declaration of Prof. Steve Rannard dated Oct. 27, 2019 filed in EP 15725209.9.
English Summary of Examination Report CN (China) 201480042200.1, dated Jan. 29, 2020.
English Summary of Examination Report QA (Qatar) QA/201601/00021, dated Dec. 12, 2019.
English Summary of Office Action HN (Honduras) 2016002313, dated Feb. 11, 2020.
English Summary of Office Action ID (Indonesia) P00 201608726, dated Oct. 17, 2019.
English Summary of Office Action MX (Mexico) MX/a/2016/014917, dated Feb. 25, 2020.
English Translation of Examination Report PE (Peru) 0001022016/DIN, dated Jan. 15, 2020.
Examination report regarding GB (Great Britain) 1605346.4, dated Nov. 13, 2018.
Examination report regarding GB (Great Britain) 1813313.2, dated Jan. 14, 2019.
KIPO Brief in Appeal of Cancellation Decision with English Translation dated Jan. 13, 2020.
Printout of the webpage http://www.olaplex.com/pages/patent, taken on Sep. 22, 2016.
Third Party Observation CA (Canada) 2947303, dated Jan. 14, 2020.
Office Action Japanese Appeal No. 2018-15999; JP (Japan) 2016-572832 dated Nov. 19, 2019 with English Translation.
Olaplex Bond Mulitplier No. 1 Mix with Highlights, balayage, or high lift color label (Jun. 2014).
Olaplex, Apparent description of booth presentation during Bronner Bros. show in Atlanta http://www.instagram.com/p/zacpQuIJfn/, Instagram post Feb. 22, 2015.
Ruetsch, et al., "Photodegradation of human air: An SEM study", J. Cosmet. Sci., 51:101-125 (2000).
Third Party Observation JP (Japan) 2016-572832 with English Translation dated Apr. 19, 2019.
Voet, et al., Fundamentals of Biochemistiy Excerpt (2008).
Yang, et al., "Polymerization of Maleic Acid and Itaconic Acid Studied by FT-Raman Sectroscopy", J. Applied Polymer Science, 81:223-228 (2001).
2019 Heo3618 appeal of Korean Patent Cancellation Defendant-Inventor Reference Brief (with English Translation) filed Nov. 12, 2020.
2019Heo3618 Appeal of Korean Patent Cancellation Defendant-Intervenor Reference Brief (with English translation) filed Nov. 16, 2020.
2019Heo3618 Appeal of Korean Patent Cancellation, Defendant-Intervenor Presentation (with English translation) dated Sep. 23, 2020.
2019Heo3618 Appeal of Korean Patent Cancellation, Defendant-Intervenor Reference Brief (with English translation) filed Oct. 27, 2020.
2019Heo3618 Appeal of Korean Patent Cancellation, Expert Declaration of Dr. Steve Rannard signed Dec. 25, 2019.
2019Heo3618 Appeal of Korean Patent Cancellation, Expert Declaration of Dr. Steve Rannard signed Jun. 9, 2020.
2019Heo3618 Appeal of Korean Patent Cancellation, Expert Declaration of Dr. Steve Rannard signed Nov. 4, 2020.
2019Heo3618 Appeal of Korean Patent Cancellation, KIPO Defendant Brief (with English translation) dated Sep. 18, 2020.
2019Heo3618 Appeal of Korean Patent Cancellation, KIPO Defendant Presentation (with English Translation) dated Sep. 23, 2020.
2019Heo3618 Korean Court Decision (with English Translation) dated Feb. 3, 2021.
Brief English Summary of Office Action IL (Israel) Application No. 265590 dated Sep. 23, 2020.
Catzy Blonde translation filed Feb. 2, 2018.
Certified English Translation of DE1220969 dated Dec. 13, 2016.
Certified English Translation of KR2006-0059564 dated Dec. 30, 2016.
Declaration of Dr. Robert J.W. Hefford filed in Application No. AU2017251818 signed Jul. 27, 2020.
Declaration of Dr. Robert J.W. Hefford filed in Application No. EP3142637 signed Apr. 10, 2020.

(56) References Cited

OTHER PUBLICATIONS

Declaration of Dr. Steve Rannard filed in Application No. AU2017251818 signed Nov. 9, 2020.
Declaration of Hiroshi J. Sheraton filed in Application No. AU2017251818 signed Jul. 28, 2020.
Declaration of Hiroshi J. Sheraton filed in Application No. EP3142637 signed Jul. 8, 2020.
Declaration of Robert Vernon Law filed in Application No. AU2017251818 signed Jul. 20, 2020.
English Summary of IL (Israel) Application No. 265590 dated Mar. 13, 2020.
English Summary of MY (Malaysia) Application No. PI 2016704186 Office Action dated Oct. 26, 2020.
English Summary of Notice of Re-Examination CN (China) Application No. 201580026038.9 dated Dec. 10, 2020.
English Translation of 2019Heo3618 Appeal of Korean Patent Cancellation, Defendant-Inventor Brief dated Sep. 16, 2020.
English Translation of PE (Peruvian) Office Action Application No. 002238-2016/DIN dated Sep. 7, 2020.
English Translation of PE (Peruvian) Office Action Application No. 002238-2016/DIN dated Feb. 19, 2021.
English Translation of Third Party Observation BR (Brazil) Application No. 1120160263782 dated Mar. 17, 2020.
Extended European Search Report EP (Europe) Application No. 20178358.6 dated Jan. 13, 2021.
JOICO Verolight Powder Bleach and Verolight Plus MSDS dated Feb. 10, 2013.
Memorandum in Response to Official Action of Oct. 7, 2018 in Israel application No. 248989 dated Jan. 24, 2019.
Mintel database entry for Bigen Permanent Powder Hair Colour (Jun. 2013).
Mintel database entry for Samy Fat Foam product (Oct. 2010).
Notice of Intention to refuse Supplementary Examination Report SG (Singapore) Application No. 11201609005Q dated Jan. 7, 2021.
Notice of Opposition in EP (Europe) European Application No. EP 16720308.2 dated Jul. 14, 2020.
Notice of Opposition in EP (Europe) European Application No. EP 3142637 dated Jul. 29, 2020.
Office Action CN (China) Application No. 201480042200.1 dated Dec. 9, 2020 with English Summary.
Office Action CN (China) Application No. 201580026038.9 dated Nov. 25, 2020 with English Summary.
Office Action CR (Costa Rica) Application No. 20160053 dated Dec. 9, 2020 with English Summary.
Office Action HN (Honduras) Application No. 2016-002313 dated Dec. 23, 2020 with English Summary.
Office Action JP (Japan) Japanese Application No. 2017-555304 dated Mar. 18, 2020 with English Summary.
Office Action JP (Japan) Japanese Office Action for Japanese Application No. 2017-555304 dated Nov. 30, 2020 with English Summary.
PGR 2018-00023—Wickett, Randall Declaration dated Jan. 31, 2018.
PGR 2018-00023 Redacted Petition for Post-Grant review of U.S. Pat. No. 9,668,954 dated Jan. 31, 2018.
PGR 2018-00024—Wickett, Randall Declaration dated Jan. 31, 2018.
PGR 2018-00024 Redacted Petition for Post-Grant review of U.S. Pat. No. 9,668,954 dated Jan. 31, 2018.
PGR 2018-00025—Wickett, Randall Declaration Feb. 15, 2019.
PGR 2018-00025 Petition for Post-Grant review of U.S. Pat. No. 9,668,954 (REDACTED) dated Feb. 1, 2018.
Product Information for Maxton Bleach Powder (May 2006).
Redken Flash Lift Lightening Powder Label and Instructions May 21, 2018.
Statement of Grounds and Particulars in Opposition Proceeding in AU (Australia) Application No. 2017251818 filed May 1, 2020.
Third Party Observation filed in ID (Indonesia) Application No. 2017/09919 dated May 19, 2020.
Third Party Observation filed in IL (Israel) Application No. 265590 dated Mar. 26, 2020.
Third Party Observation filed in NZ (New Zealand) Application No. 725652, dated Mar. 5, 2021.
Third Party Observation filed in SG (Singapore) Application No. 11201609005Q dated Apr. 5, 2019.
Third Party Observation filed in SG (Singapore) Application No. 11201609005Q dated Dec. 27, 2018.
Third Party Observation filed in SG (Singapore) Application No. 11201609005Q dated Dec. 8, 2017.
Third Party Observation filed in SG (Singapore) Application No. 11201609005Q dated Feb. 15, 2018.
Third Party Observation filed in SG (Singapore) Application No. 11201609005Q dated May 25, 2018.
Written Opinion for SG (Singapore) Application No. 11201609005Q dated May 7, 2020.

\* cited by examiner

METHODS FOR TREATING RELAXED HAIR

CROSS-REFERENCE TO RELATED APPLICATION

This application is a continuation of U.S. Ser. No. 15/626,453, filed Jun. 19, 2017, which is a continuation of U.S. Ser. No. 15/341,893, filed Nov. 2, 2016, now U.S. Pat. No. 9,717,668 issued Aug. 1, 2017, which is a divisional of U.S. Ser. No. 15/137,788, filed Apr. 25, 2016, now U.S. Pat. No. 9,597,273, which claims benefit of and priority to U.S. Provisional Application No. 62/152,220, filed Apr. 24, 2015, which are incorporated herein by reference in their entirety.

FIELD OF THE INVENTION

The present invention generally relates to compositions and methods for treating hair, particularly for repairing disulfide bonds in hair treated with a lye or alkali-based relaxer and for controlling the level of curl retention in the relaxed hair.

BACKGROUND OF THE INVENTION

Hair consists of many long, parallel chains of amino acids. These chains, or polymers, of amino acids are bound to each other via 1) hydrogen bonding, 2) salt bridges between acid and base groups, and 3) disulfide bonds.

At alkaline pH, the disulfide bonds in hair can be broken (Dombrink et al., *Chem Matters*, 1983, page 8). For example, lye-based relaxers contain hydroxide ions which attack the disulfide linkages. The disruption of disulfide bonds by the lye-based relaxer is used to achieve straightening of the hair through changing of the relative positions of opposing polypeptide chains. The straightening process is completed by rinsing the hair and/or application of a neutralizing composition.

While lye and other alkali-based relaxers are highly effective at relaxing and straightening hair they can result in reduction of hair strength and potential loss of hair through breakage. Relaxing hair can therefore be viewed as a destructive and irritating process which can strip hair of its natural fatty acids. Exposing hair to alkaline conditions also damages the hair and further causes the cuticle or outer surface of the hair strands to become roughened and can result in ruffled, tangled, and generally unmanageable hair. Roughened hair catches light unevenly and makes the hair look lusterless and dull. The hair can also be left with increased levels of static upon drying, which can interfere with combing and result in a condition commonly referred to as "fly-away hair."

A variety of approaches have been developed to alleviate these problems, including post-shampoo application of hair conditioners, such as leave-on and rinse-off products. Typically, conditioning rinses put back the oily coating, especially to the damaged portion of the hair where the cuticle has become ruffled since conditioners cling best to these portions. However, too much or too heavy a conditioner will make the hair stickier, thus attracting dirt and often may make more shampooing treatments necessary.

Yet another issue with the use of lye and other alkali-based hair relaxers is that their application leads to completely relaxed and straightened hair without any level of curl and/or any controllably retained level of curl. Furthermore, due to the reduction of hair strength and potential loss of hair due to breakage from such relaxing processes, any further application of a permanent wave process (i.e., to introduce a controlled amount of curl) to the already relaxed and straightened hair would be inadvisable as it would result in further damage and/or breakage of the hair.

Thus, there is a need for hair formulations and treatments that can provide improved conditioning benefit for hair relaxed with lye or alkali-based relaxers. Specifically, there is a need to provide long lasting moisturized feel, smooth feel, and manageability control to the treated hair when it is dried.

There is also a need for hair formulations and treatments that repair and/or strengthen damaged hair treated with lye or alkali-based relaxing agents or hydroxide-containing relaxing agents.

There is also a need for hair formulations and treatments that afford the ability to tune or select the level of curl achieved and/or retained in hair which has been relaxed with lye or alkali-based relaxing agents or hydroxide-containing relaxing agents.

Therefore, it is an object of this invention to provide improved compositions and methods for repairing and/or strengthening hair treated with lye or alkali-based relaxing agents or hydroxide-containing relaxing agents.

It is a further object of this invention to provide compositions and methods which can be used to tune or select the level of curl achieved and/or retained in hair that has been treated with lye or alkali-based relaxing agents or hydroxide-containing relaxing agents.

SUMMARY OF THE INVENTION

Compositions, kits, and methods for repairing bonds, for example, disulfide bonds, in relaxed hair that has been damaged by treatment with a lye or alkali-based relaxing agent(s) or hydroxide-containing relaxing agents. The compositions, kits, and methods can also be used to control the level of curl retention during the relaxing process.

Active agent formulations, which contain one or more compounds that interact with keratin through one or more binding events (e.g., absorption, binding, etc.) which may involve reaction with one or more thiols in the hair are described herein. "Binding" as used herein refers to the formation of covalent, ionic, or hydrogen bonds. The active agent compositions can provide improved conditioning and provide long lasting moisturized feel and smooth feel without leaving the hair greasy, improve appearance (e.g., sheen), increase dry strength (tensile strength), ease combing of the hair when wet or dried, reduce hair breakage, or decrease frizz, or any combination thereof.

Without being bound by theory, it is believed that use of the active agent formulations prevents reversion of the hair's repaired bonds to their free thiol state, for at least one week, two weeks, three weeks, four weeks, one month, or two months, or longer, after application of the composition.

Traditional methods of straightening hair make use of lye or alkali-based relaxers or hydroxide-containing relaxing agents which can result in reduction of hair strength and potential loss of hair through breakage. The methods disclosed herein use active agents which can repair damage to relaxed hair and also provide improved methods of styling hair, such as during a hair relaxing/straightening treatment using lye or alkali-based relaxers or hydroxide-containing relaxing agents.

The active agent formulations can be applied during the hair relaxing treatment along with the relaxing agent. Without wishing to be bound by any particular theory, the addition of the active agents described herein simultaneously with a lye or alkali-based relaxing agent or hydroxide-containing relaxing agent can be used to tune or control the level of curl retention in the relaxed hair. The level of curl retention can depend on the amount of active agent(s) used, which can be represented as a weight ratio of active agent present in the hair relaxing to the amount of lye or alkali-based relaxing agent present. Typically, the greater the amount of active agent present in the relaxing formulation the greater the level of curl retention. In some embodiments, the weight ratio of the relaxing agent formulation to the active agent formulation is in the range of about 1:10 to about 10:1. The inclusion of the one or more active agents permits not only control of the level of curl retention during hair relaxation but further allows for repair of the disulfide bonds broken during the relaxation process to otherwise prevent damage caused by the relaxing agent(s).

In some other embodiments, the active agent formulations can be applied immediately following the application of the lye or alkali-based relaxing agent(s) or hydroxide-containing relaxing agents.

DETAILED DESCRIPTION OF THE INVENTION

I. Definitions

Numerical ranges disclosed herein disclose individually each possible number in such range, as well as any sub-ranges and combinations of sub-ranges encompassed therein. For example, a carbon range (i.e., $C_1$-$C_{10}$) is intended to disclose individually every possible carbon value and/or sub-range encompassed within. For example, a carbon length range of $C_1$-$C_{10}$ discloses $C_1$, $C_2$, $C_3$, $C_4$, $C_5$, $C_6$, $C_7$, $C_8$, $C_9$, and $C_{10}$, as well as discloses sub-ranges encompassed within, such as $C_2$-$C_9$, $C_3$-$C_8$, $C_1$-$C_5$, etc. Similarly, an integer value range of 1-10 discloses the individual values of 1, 2, 3, 4, 5, 6, 7, 8, and 10, as well as sub-ranges encompassed within. Further, a concentration range or weight percent range, such as from 1% to 2% by weight of the formulation discloses, the individual values and fractions thereof, such as 1%, 1.1%, 1.2%, 1.32%, 1.48% etc., as well as sub-ranges encompassed within.

The term "hair" refers to one or more than one strand of hair, as well as the natural components of hair, such as oil from a body. Hair also refers to virgin hair or processed hair, for example hair that has been exposed to hair waving or hair straightening formulations.

An "effective amount", e.g., of the active agent or compositions described herein, refers to an amount of the active agent in a composition or formulation which, when applied as part of a desired hair treatment achieves the desired result, such as curl retention, smoothness, little or no breakage, great or good feel, and/or healthy appearance by visual inspection.

"Cosmetically acceptable" refers to those compounds, materials, and compositions, which are, within the scope of sound medical judgment, suitable for use in contact with the tissues of human beings and animals without excessive toxicity, irritation, allergic response, or other problems or complications commensurate with a reasonable benefit/risk ratio. More specifically, cosmetically acceptable refers to a material, compound, or composition which is suitable for use in contact with the skin, scalp, or hair. Cosmetically acceptable materials are known to those of ordinary skill in the art.

"Shampoo", as used herein, generally refers to a liquid or semi-solid formulation applied to the hair that contains detergent or soap for washing the hair.

"Conditioner", as used herein, generally refers to a formulation (e.g., liquid, cream, lotion, gel, semi-solid) applied to the hair to soften the hair, smooth the hair, and/or change the sheen of the hair.

"Analog" and "Derivative" are used herein interchangeably and refer to a compound that possesses the same core as the parent compound, but differs from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

"Electrophilic group" or "electrophilic moiety" are used interchangeably and refer to one or more functional groups or moieties that have an affinity for or attract electrons.

"Michael acceptor", as used herein, is a species of electrophilic groups or moieties that participates in nucleophilic addition reactions. The Michael acceptor can be or can contain an α,β-unsaturated carbonyl-containing group or moiety, such as a ketone. Other Michael acceptors include pi-bonds, such as double or triple bonds conjugated to other pi-bond containing electron withdrawing groups, such as nitro groups, nitrile groups, and carboxylic acid groups.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. In some embodiments, the chain has 1-6 carbons. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Examples include oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic rings. The ring may be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that may include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms, such as nitrogen, may have hydrogen substituents and/or any permissible substituents of organic compounds described herein that satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Polymer", as used herein, refers to a molecule containing more than 10 monomer units.

"Water-soluble", as used herein, generally means at least 50, 75, 100, 125, 150, 200, 225, or 250 g is soluble in 1 L of water at 25° C.

"Relaxing agents," as used herein typically refers to hydroxide-containing compounds, such as lye or other hydroxide-containing compounds, such as ammonium hydroxide. When these hydroxide-containing compounds are present in a hair relaxing formulation the hydroxide ions produce a relaxing formulation with a high pH.

"Lye," or "lye relaxer," are used interchangeably herein and refer to an aqueous formulation or composition containing an alkali metal containing hydroxides (e.g. Sodium hydroxide and/or Potassium hydroxide).

II. Active Agent Formulations

The active agent formulations disclosed herein are concerned with treating hair which is either in the process of being relaxed or has undergone a relaxing treatment with a relaxing agent containing formulation. Additionally, the active agent formulations, when used during the relaxing treatment can be used to control, select, or tune the level of curl achieved and/or retained in the relaxed hair, as compared to the hair's natural unrelaxed state. The level of curl retention depends on the amount of one or more active agents applied, which can be represented as a weight ratio of the weight of one or more active agents (or the weight of the active agent containing formulation) to the weight of the hair relaxing formulation. Typically, the greater the amount of active agent present in the relaxing formulation the greater the level of curl retention which can be achieved. Furthermore, the inclusion of one or more active agents, as described herein, permits control of the level of curl retention during hair relaxation while reducing hair breakage and damage during the relaxation process caused by the relaxing agent(s).

The formulations contain one or more active agents (also referred to herein as "compounds" or "active agents") which can be combined with one or more cosmetically acceptable carriers and/or excipients that are considered safe and effective to human hair and/or human scalp, and may be administered to an individual's hair without causing undesirable biological side effects, such as burning, itching, and/or redness, or similar adverse reactions.

The active agent is typically present in an amount ranging from about 0.01 wt % to about 50 wt % of the formulation, preferably from about from about 1 wt % to about 25 wt % of the formulation, more preferably from about 1 wt % to about 15 wt %, most preferably from about 1 wt % to about 10 wt %. Typically, the active agent may be present in an amount ranging from about 1 to about 5 wt % of the formulation.

The active agent is stable in aqueous solution for a period of at least 2, 3, 4, 5, 6, 8, 9, 10, 11, or 12 months or longer at pH of 3 to 8, preferably 3 to 5, and a temperature of about 25-30° C., preferably about 25° C. "Stable" as used herein with respect to shelf-life means that at least 40, 45, 50, 55, 60, 65, 70, 75, 80, 85, 90, or 95% of the compound is unchanged over the specified time period.

a. Active Agent

The active agent contains at least one reactive moiety capable of reacting with and forming bonds with a nucleophile, such as a thiol. The active agents optionally contain a linker group. The reactive moieties, upon reaction with thiol groups on the hair follicle, form bonds that are stable, for example, hydrolytically stable. "Stable", as used in reference to the bonds formed between thiol groups on hair follicles means the bonds remain intact for at least one week, two weeks, three weeks, four weeks, one month, or two months or longer when exposed to water at a pH of 3 to 8, preferably at a pH of 3 to 5, at a temperature from about 5° C. to about 100° C., from about 20° C. to about 75° C., more preferably from about 20° C. to about 50° C., from about 25° C. to about 40° C., or from about 25° C. to about 30° C., and more preferably at a temperature of about 25° C. In some embodiments, the temperature is about 25° C. It is also preferred that the reaction between the reactive moieties and thiol occur around room temperature, for example, from about 15° C. to about 35° C., preferably from about 20° C. to about 30° C., more preferably from about 22° C. to about 27° C.

i. Active Agents Defined by Formula I

In some embodiments, the binding agents have a structure according to Formula I:

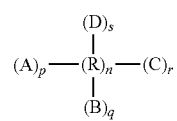

Formula I wherein

A, B, C, and D are reactive moieties containing one or more charges,

R is a linker that contains two or more charges, wherein the charges are opposite to the charges on the reactive moieties, wherein n=1-100, preferably n=1-10, more preferably n=1; and each occurrence of p, q, r, and s is independently an integer from 0 to 25, preferably from 0 to 10, more preferably from 0 to 2. The sum of p+q+r+s is equal to or greater than 2.

The reactive moieties may be present on any atom of the linker. In some embodiments, the reactive moieties are the same. In some embodiments, one or more of the reactive moieties is different.

In some embodiments, the reactive moieties are negatively charged and the linker or spacer has positively charged moieties. In other embodiments, the reactive moieties are positively charged and the linker or spacer has negatively charged moieties. Generally, the sum of the charges on the binding agent of Formula I is zero through stoichiometric imbalances may exist.

The reactive moieties on the binding agents are preferably linked via a linker R. The linker R, as used herein, refers to one or more polyfunctional, e.g. bifunctional molecules, trifunctional molecules, tetrafunctional molecules, etc., which can be used to ionically bound the two or more reactive moieties and which do not interfere with the reactive properties of the binding agents. The reactive moieties may be attached to any part of linker R.

1. Linker R

In a preferred embodiment, in Formula I, n=1 and the linker R is not a polymer. The linker R can be a single atom, such as a heteroatom (e.g., O or S), a group of atoms, such as a functional group (e.g., amine, —C(=O)—, —CH$_2$—), or multiple groups of atoms, such as an alkylene chain. Suitable linkers include but are not limited to oxygen, sulfur, carbon, boron, nitrogen, alkoxy, alkyl, alkenyl, cycloalkyl, cycloalkenyl, aryl, heterocycloalkyl, heteroaryl, ether, amine, and a polymer.

The linker R is optionally independently substituted with one or more substituents including hydrogen, halogen, cyano, alkoxy, alkyl, alkenyl, cycloalkyl, cycloalkenyl, aryl, heterocycloalkyl, heteroaryl, amine, hydroxy, formyl, acyl, carboxylic acid (—COOH), —C(O)R$^1$, —C(O)OR$^1$, carboxylate (—COO—), primary amide (e.g., —CONH$_2$), secondary amide (e.g., —CONHR$^1$), —C(O)NR$^1$R$^2$, —NR$^1$R$^2$, —NR$^1$S(O)$_2$R$^2$, —NR$^1$C(O)R$^2$, —S(O)$_2$R$^2$, —SR$^1$, and —S(O)$_2$NR$^1$R$^2$, sulfinyl group (e.g., —SOR$^1$), and sulfonyl group (e.g., —SOOR$^1$); wherein R$^1$ and R$^2$ may each independently be hydrogen, alkyl, alkenyl, alkynyl, cycloalkyl, aryl, heterocycloalkyl and heteroaryl; wherein each of R$^1$ and R$^2$ is optionally independently substituted with one or more substituents selected from the group consisting of halogen, hydroxyl, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or =O or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl.

In some embodiments, the linker R may be an alkoxy, ether, alkyl, alkenyl, cycloalkyl, cycloalkenyl, aryl, heterocycloalkyl, heteroaryl, amine, or a polymer.

2. Active Agents According to Formula I

The active agent according to Formula I contains at least two reactive moieties that are capable of reacting with thiols or amines to form covalent bonds. For example, the reactive moieties are capable of reacting with a thiol group in the hair to form a stable covalent bond. The reactive moiety is typically an electrophilic moiety capable of forming a salt with the linker. Alternately, the reactive moiety can be capable of reacting with a free radical.

The active agent according to Formula I contains at least two reactive moieties. However, the binding agent may contain three, four, five, six, or greater than six reactive moieties.

The reaction between the reactive moiety and the thiol groups may be initiated at room temperature and pressure when the reactive moiety contacts a thiol group in the hair. In some embodiments, the reaction may require an initiator, such as heat, catalyst, basic conditions, or a free radical initiator. The rate of reaction between the reactive moiety and the thiol may be increased by changes in temperature, pH, and/or addition of one or more excipients, such as a catalyst; however, this is generally not required.

The two or more reactive moieties on the binding agent can be the same. In some embodiments, the two or more reactive moieties are different.

In some embodiments, the reactive moieties are capable of undergoing a conjugate additional reaction. The reactive moieties can independently be or contain a Michael acceptor, a succinimidyl-containing group, a maleimido-containing group, azlactone, a benzoxazinone derivative, vinyl sulfone, vinyl sulfoximine, vinyl sulfonate, vinyl phosphonate, benzoxazinone, isocyanate, epoxide, an electrophilic moiety containing a leaving group, an electrophilic thiol acceptor, acrylic or acrylate group, a methacrylic or methacrylate group, a styrene group, an acryl amide group, a methacryl amide group, a maleate group, a fumarate group, an itaconate group, a vinyl ether group, an allyl ether group, an allyl ester group, a vinyl ester group, a sulfonate group, a phosphonate group, a sulfoxide group, a sulfonamide group, a sulfinimide group, a sulfinamide group, a sulfonimidate group, or a sulfonimidamide group.

In the preferred embodiments, each of reactive moieties A, B, C, and/or D when present independently contains a moiety selected from the group consisting of a vinyl sulfone, an acrylate group, a methacrylate group, a styrene group, an acryl amide group, a methacryl amide group, a maleate group, a fumarate group, and an itaconate group. Further, in the preferred embodiments, n=1 and the linker R is not a polymer. Optionally, all of the reactive moieties are the same. For example, in some embodiments all of the reactive moieties are maleate groups.

In some embodiments, the active agent according to Formula I has one of the following structures:

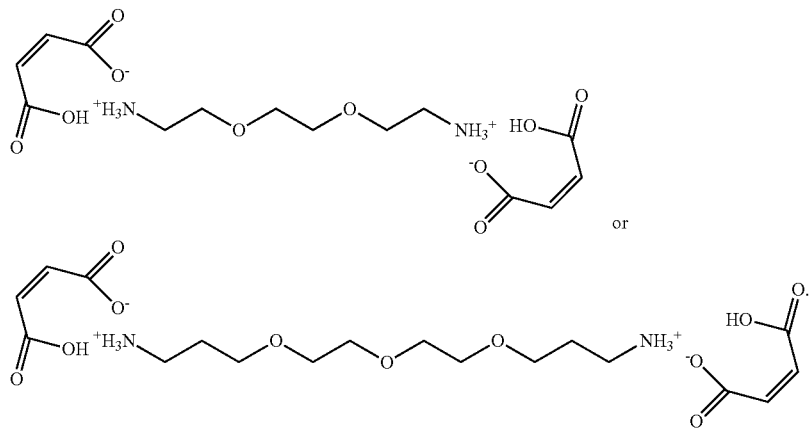

Active agents according to Formula I are further described in U.S. Patent Publication No. 2015/0034117 A1 to Pressly, et al. and issued as U.S. Pat. No. 9,095,518, which is incorporated herein by reference with respect to its disclosure of active agents.

ii. Active Agents Defined by Formula II

In some other embodiments, the active agent is a polyfunctional compound that contains ionizable functional groups capable of forming ionic bonds and functional groups capable of forming a covalent bond with a nucleophile, such as a thiol or an amine. Suitable ionizable functional groups include, but are not limited to, acidic groups such as carboxylic acids, sulfonic acids, phosphonic acids, and basic groups, such as amines. Suitable functional groups capable of forming a covalent bond with a nucleophile, such as a thiol or an amine, include, but are not limited to, Michael acceptors, alkyl halides or sulfonate esters.

The active agent may have the following Formula II:

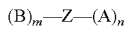  Formula II wherein Z is a linker or is absent, m and n are each an integer independently selected from 1-6, provided that m+n is at least 2, B is a functional group capable of forming a covalent bond with a thiol or amine group, and A is an ionizable functional group. Preferably, the linker Z is not a polymer.

Exemplary active agents according to Formula II may contain thiol reactive functional groups, as group B, for example, such as those shown in the following moieties:

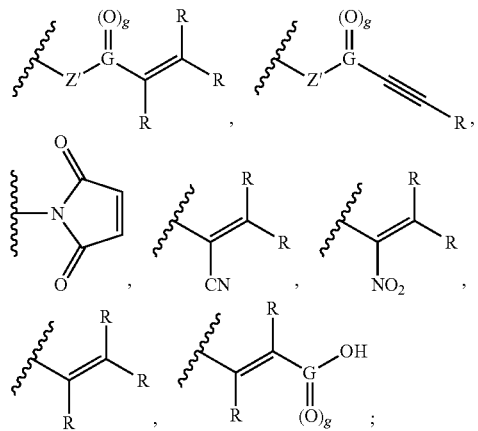

wherein R is independently selected from hydrogen, $C_{1-6}$ alkyl, aryl, or an ionizable functional group; Z' is oxygen (O), NH, or is absent; and G is carbon (C) and g is 1, or G is sulfur (S) and g is 2. In preferred embodiments, Z is a linker or is absent, the linker is not a polymer, and group B is a functional group capable of forming a covalent bond with a thiol or amine group and group B is independently selected from the group consisting of:

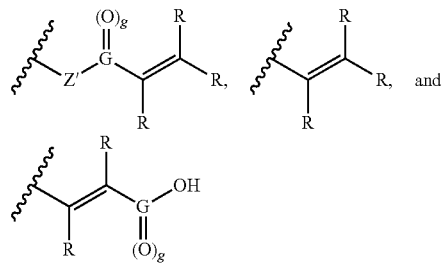

wherein R, Z', G, and g are as previously defined.

1. Linker Z

The linker Z, when present, can be or can contain an alkyl, alkenyl, cycloalkyl, cycloalkenyl, aryl, heterocycloalkyl or heteroaryl group. One or more of the carbon atoms in the alkyl, alkenyl, cycloalkyl, cycloalkenyl, and aryl groups can be substituted with a heteroatom, yielding, for instance, an ether or alkylamine-containing linker.

The linker Z may optionally be substituted with one or more substituents, which may be the same or different, including hydrogen, halogen, cyano, alkoxy, alkyl, alkenyl, cycloalkyl, cycloalkenyl, aryl, heterocycloalkyl, heteroaryl, amine, hydroxy, oxo, formyl, acyl, carboxylic acid (—COOH), —C(O)R$^1$, —C(O)OR$^1$, carboxylate (—COO—), primary amide (e.g., —CONH$_2$), secondary amide (e.g., —CONHR$_{11}$), —C(O)NR$^1$R$^2$, —NR$^1$R$^2$, —NR$^1$S(O)$_2$R$^2$, —NR$^1$C(O)R$^2$, —S(O)$_2$R$^2$, —SR$^1$, and —S(O)$_2$NR$^1$R$^2$, sulfinyl group (e.g., —SOR$_1$), and sulfonyl group (e.g., —SOOR$_1$); wherein R$^1$ and R$^2$ may each independently be hydrogen, alkyl, alkenyl, alkynyl, cycloalkyl, aryl, heterocycloalkyl and heteroaryl; wherein each of R$^1$ and R$^2$ is optionally independently substituted with one or more substituents selected from the group consisting of halogen, hydroxyl, oxo, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or oxo or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl.

In certain preferred embodiments, the linker Z is a $C_{1-10}$ alkyl group which may be unsubstituted or substituted one or more times by oxo, hydroxyl, carboxyl, amido or amino. Preferably, the linker Z is a $C_{1-4}$ alkyl group. The alkyl group may be linear or branched. The alkyl group may also be interrupted one or more times by a heteroatom selected from oxygen, sulfur and nitrogen. An example of such a di-carboxylic acids having a heteroatom interruption is thiodipropionic acid. In other embodiments, the alkyl group may contain one or more double or triple bonds.

In some embodiments, the active agent according to Formula II has one of the following structures:

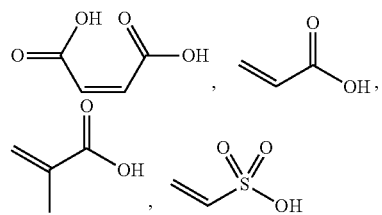

or is a simple salt of these structures.

iii. Active Agents Defined by Formula III

In certain other embodiments, the active agent may have the following Formula III:

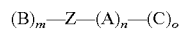  Formula III wherein Z is a linker or is absent, m and n are each an integer independently selected from 1-6, provided that m+n is at least 2, B is a functional group capable of forming a covalent bond with a nucleophile, such a thiol or amine group, A is an ionizable functional group as defined above, and C is an ionic group which is also capable of forming a covalent bond with a thiol and which has a charge opposite to that of ionizable group A. Group C is ionically bonded (denoted by dashed line) to group A. For ionic group C, o is an integer value independently selected from 1-6, such that the sum of charges of group C and ionizable group A is zero. Preferably linker Z is not a polymer.

In active agents of Formula III, group C is an ionic group which is ionically bonded to ionizable group A and contains at least one thiol reactive. Group C may be a Michael acceptor, a succinimidyl-containing group, a maleimido-containing group, azlactone, a benzoxazinone derivative, vinyl sulfone, vinyl sulfoximine, vinyl sulfonate, vinyl phosphonate, benzoxazinone, isocyanate, epoxide, an electrophilic moiety containing a leaving group, an electrophilic thiol acceptor, acrylic or acrylate group, a methacrylic or methacrylate group, a styrene group, an acryl amide group, a methacryl amide group, a maleate group, a fumarate group, an itaconate group, a vinyl ether group, an allyl ether group, an allyl ester group, a vinyl ester group, a sulfonate group, a phosphonate group, a sulfoxide group, a sulfonamide group, a sulfinimide group, a sulfinamide group, a sulfonimidate group, or a sulfonimidamide group.

The active agents according to Formula III may contain thiol reactive functional groups which react with a nucleophile, such as a thiol, as group B.
Exemplary thiol reactive functional groups include, but are not limited, to those shown in the following moieties:

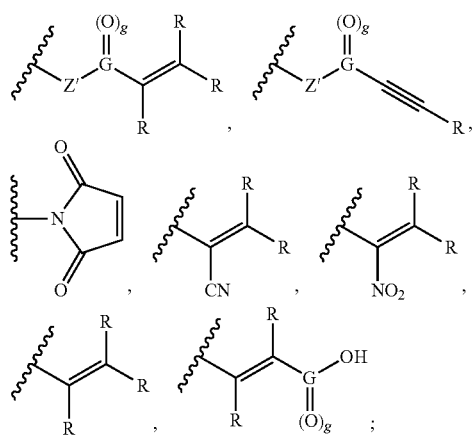

wherein R is independently selected from hydrogen, $C_{1-6}$ alkyl, aryl, or an ionizable functional group; Z' is oxygen (O), NH, or is absent; and G is carbon (C) and g is 1, or G is sulfur (S) and g is 2. In preferred embodiments, Z is a linker or is absent, the linker is not a polymer, and group B is a functional group capable of forming a covalent bond with a thiol or amine group and group B is independently selected from the group consisting of:

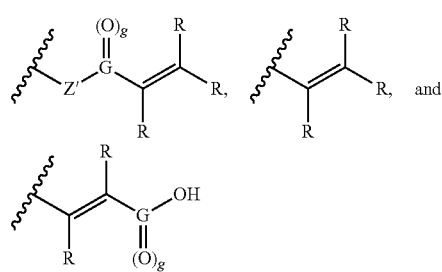

wherein R, Z', G, and g are as previously defined.

1. Linker Z

The linker Z, when present, can be or can contain an alkyl, alkenyl, cycloalkyl, cycloalkenyl, aryl, heterocycloalkyl or heteroaryl group. One or more of the carbon atoms in the alkyl, alkenyl, cycloalkyl, cycloalkenyl, and aryl groups can be substituted with a heteroatom, yielding, for instance, an ether or alkylamine-containing linker.

The linker Z may optionally be substituted with one or more substituents, which may be the same or different, including hydrogen, halogen, cyano, alkoxy, alkyl, alkenyl, cycloalkyl, cycloalkenyl, aryl, heterocycloalkyl, heteroaryl, amine, hydroxy, oxo, formyl, acyl, carboxylic acid (—COOH), —C(O)$R^1$, —C(O)O$R^1$, carboxylate (—COO—), primary amide (e.g., —CONH$_2$), secondary amide (e.g., —CONHR$_{11}$), —C(O)NR$^1$R$^2$, —NR$^1$R$^2$, —NR$^1$S(O)$_2$R$^2$, —NR$^1$C(O)R$^2$, —S(O)$_2$R$^2$, —SR$^1$, and —S(O)$_2$NR$^1$R$^2$, sulfinyl group (e.g., —SOR$_1$), and sulfonyl group (e.g., —SOOR$_1$) wherein $R^1$ and $R^2$ may each independently be hydrogen, alkyl, alkenyl, alkynyl, cycloalkyl, aryl, heterocycloalkyl and heteroaryl; wherein each of $R^1$ and $R^2$ is optionally independently substituted with one or more substituents selected from the group consisting of halogen, hydroxyl, oxo, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or oxo or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl and dialkylaminocarbonyl.

In certain preferred embodiments, the linker Z is a $C_{1-10}$ alkyl group which may be unsubstituted or substituted one or more times by oxo, hydroxyl, carboxyl, amido or amino. Preferably, the linker Z is a $C_{1-4}$ alkyl group. The alkyl group may be linear or branched. The alkyl group may also be interrupted one or more times by a heteroatom selected from oxygen, sulfur and nitrogen. An example of such a di-carboxylic acids having a heteroatom interruption is thiodipropionic acid. In other embodiments, the alkyl group may contain one or more double or triple bonds.

In some embodiments, the active agent of Formula III has one of the following structures:

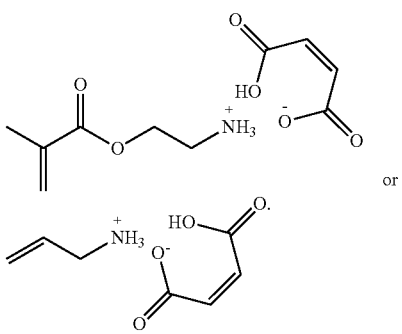

b. Excipients

The active agent formulations can typically contain one or more cosmetically acceptable excipients. Cosmetically acceptable excipients include, but are not limited to, water, preservatives, antioxidants, chelating agents, sunscreen agents, vitamins, dyes, hair coloring agents, proteins, amino acids, natural extracts such as plant extracts, humectants, fragrances, perfumes, oils, emollients, lubricants, butters, penetrants, thickeners, viscosity modifiers, polymers, resins, hair fixatives, film formers, surfactants, detergents, emulsifiers, opacifying agents, volatiles, propellants, liquid vehicles, carriers, salts, pH adjusting agents (e.g., citric acid), neutralizing agents, buffers, hair conditioning agents, anti-static agents, anti-frizz agents, anti-dandruff agents, absorbents, and combinations thereof.

The formulations may contain one or more cosmetically acceptable excipients. In some forms, the formulations contain the active agent, water, and optionally a preservative and/or fragrance.

The formulation for treating hair during or immediately following a relaxation process with a relaxing formulation may be in any suitable physical form. Suitable forms include, but are not limited to low to moderate viscosity liquids, lotions, milks, mousses, sprays, gels, creams, shampoos, conditioners, and the like. Suitable excipients, such as those listed above, are included or excluded from the hair care formulation depending on the form of use of the formulation (e.g., hair spray, cream, conditioner, or shampoo).

The cosmetically acceptable excipient is typically present in an amount ranging from about 10 wt % to about 99.99 wt % of the formulation, preferably about 40 wt % to about 99 wt %, more preferably from about 80 wt % to about to about 99 wt %.

i. Surfactants

Surfactants are surface-active agents that are able to reduce the surface tension of water and cause the formulation to slip across or onto the hair. Surfactants may also include detergents and soap. The surfactants may be amphoteric, anionic, or cationic. Suitable surfactants that may be used in the formulation include, but are not limited to, 3-aminopropane sulfonic acid, almond amide, almond amidopropyl betaine, almond amidopropylamine oxide, aluminum hydrogenated tallow glutamate, aluminum lanolate, aminoethyl sulfate, aminopropyl lauryl glutamine, ammonium $C_{12-15}$ alkyl sulfate, ammonium $C_{12-15}$ pareth sulfate, ammonium $C_{12-16}$ alkyl sulfate, ammonium $C_{9-10}$ perfluoroalkylsulfonate, ammonium capryleth sulfate, ammonium capryleth-3 sulfate, ammonium monoglyceride sulfate, ammonium sulfate, ammonium isothionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide, apricot amidopropyl betaine, arachideth-20, avocadamide, avocadamidopropyl betaine, babassuamide, babassuamidopropyl betaine, babassuamidopropylamine oxide, behenalkonium chloride, behenamide, behenamide, behenamidopropyl betaine, behenamine oxide, sodium laureth sulfate, sodium lauryl sulfate, a polyoxyether of lauryl alcohol or ceteareth-20, or combinations thereof.

Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-β-iminodipropionate, myristoamphoacetate, lauryl betaine and lauryl sulfobetaine.

More than one surfactant may be included in the formulation.

The surfactants are optionally included in an amount ranging from about 0.1% to about 15% by weight of the formulation, preferably about 1% to about 10% by weight of the formulation.

ii. Emollients

Emollient refers to a material that protects against wetness or irritation, softens, soothes, coats, lubricates, moisturizes, protects, and/or cleanses the skin. Suitable emollients for use in the formulations include, but are not limited to a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, or a combination thereof. More than one emollient may be included in the formulation.

The emollient is optionally included in an amount ranging from about 0.5% to about 15% by weight of the formulation, preferably from about 1% to about 10% by weight of the formulation.

iii. Emulsifiers

The formulations may also contain one or more emulsifiers. Suitable emulsifiers include, but are not limited to, copolymers of an unsaturated ester and styrene sulfonate monomer, cetearyl alcohol, glyceryl ester, polyoxyethylene glycol ether of cetearyl alcohol, stearic acid, polysorbate-20, ceteareth-20, lecithin, glycol stearate, polysorbate-60, or polysorbate-80, or combinations thereof. More than one emulsifier may be included in the formulation.

The emulsifier is optionally included in an amount ranging from about 0.05% to about 15% by weight of the formulation, preferably from about 0.1% to about 10% by weight of the formulation.

iv. Preservatives

One or more preservatives may be included in the formulations to prevent microbial growth in the formulations. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediaminetetraacetic acid (EDTA), potassium sorbate, and/or grapefruit seed extract, or combinations thereof. More than one preservative may be included in the formulation. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium—15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The preservative is optionally included in an amount ranging from about 0.1% to about 5% by weight of the formulation, preferably from about 0.3% to about 3% by weight of the formulation. Preferably, the formulations are paraben free.

v. Conditioning Agents

One or more conditioning agents may be included in the formulations. Suitable conditioning agents include, but are not limited to, silicone-based agents (e.g., silicone quaternium-8), panthenol, hydrolyzed wheat and/or soy protein, amino acids (e.g. wheat amino acids), rice bran wax, meadowfoam seed oil, mango seed oil, grape seed oil, jojoba seed oil, sweet almond oil, hydroxyethyl behenamidopropyl dimonium chloride, aloe leaf extract, aloe barbadensis leaf juice, phytantriol, panthenol, retinyl palmitate, behentrimonium methosulfate, cyclopentasiloxane, quaternium-91, stearamidopropyl dimethylamine, and combinations thereof.

The conditioning agent(s) is optionally included in an amount ranging from about 0.1% to about 5% by weight of the formulation, preferably from about 0.3% to about 3% by weight of the formulation.

vi. Diluents

Diluent, as used herein, refers to a substance(s) that dilutes the active agent. Water is the preferred diluent. The formulations typically contains greater than one percent (wt) water, preferably greater than five percent (wt) water, more preferably greater than 50% (wt) water, and most preferably greater than 80% (wt) water. Alcohols, such as ethyl alcohol and isopropyl alcohol, may be used at low concentrations (about 0.5% by weight of the formulation) to enhance hair or skin penetration and/or reduce odor.

vii. Viscosity Modifying Agents

The formulations may contain one or more viscosity modifying agents, such as viscosity increasing agents. Classes of such agents include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

viii. Antioxidants

The formulations may contain one or more antioxidants. Examples include, but are not limited to, tocopheryls, BHT, ascorbic acid, *Camellia sinensis* leaf extract, ascorbyl palmitate, magnesium ascorbyl phosphate, carotenoids, resveratrol, triethyl citrate, arbutin, kojic acid, tetrahexydecyl ascorbate, superoxide dismutase, zinc, sodium metabisulfite, lycopene, ubiquinone, and combinations thereof.

ix. Opacifying Agents

The formulations may contain one or more opacifying agents. Opacifying agents are added to the formulations to make them opaque. Suitable opacifying agents include, but are not limited to, glycol distearate and ethoxylated fatty alcohols.

c. Forms of the Formulation i. Creams

The formulation may be in the form of a cream. The cream typically includes the active agent in a suitable carrier. The active agent may be included in any suitable concentration. Typical concentrations of the active agent in the cream range from small amounts such as approximately 0.01% (wt), preferably at least 0.1% (wt), to large amounts, such as up to 50% (wt). Preferably the cream contains the active agent in a concentration ranging from 0.1% (wt) to 5% (wt), more preferably from 0.1% wt to 3% (wt). While greater concentrations of active agent could be present in the cream, they are generally not needed to achieve the desired results.

Additionally, the cream may include an oil, a hair conditioning agent, and/or a thickening agent. The cream may also include a fragrance, a plant extract, and/or a surfactant. The cream may be packaged in a tube, tub, bottle, or other suitable container.

ii. Liquid Active Agent Formulations

In some embodiments, a liquid active agent formulation is provided, which is mixed at the time of use with a second formulation, such as for relaxing hair. In these embodiments, the liquid active agent formulation may contain any suitable concentration of active agent in a suitable carrier, typically a diluent, such as described above. The concentration of the active agent is suitable to provide a mixture with the appropriate final volume and final concentration of active agent, as desired.

For example, a liquid active agent formulation can contain a concentration of active agent ranging from about 5% (wt) to about 50% (wt) or greater. In a preferred embodiment, the liquid active agent formulation contains about 5% (wt) to 20% (wt) active agent.

For straightening applications, prior to use, a sufficient volume of a liquid active agent formulation is mixed with a sufficient volume of a relaxing agent-containing formulation to form a relaxing/straightening mixture having the desired concentration of active agent. Typical concentrations of the active agent in the relaxing mixture can range from small amounts, such as approximately at least 0.01% (wt), preferably at least 0.1% (wt), to large amounts, such as up to 50% (wt). Preferably the relaxing mixture contains the active agent in a concentration ranging from 0.1% (wt) to 5% (wt), more preferably from 1% wt to 5% (wt).

III. Relaxing Formulations

A relaxing formulation contains one or more relaxing agents for straightening hair. Without being bound by theory, it is believed that the hydroxide ions in the relaxing agents attack disulfide linkages in hair and producing reduced thiol groups. The disruption of disulfide bonds by the relaxing agents is used to achieve straightening of the hair through changing of the relative positions of opposing polypeptide chains. Relaxing agent formulations and their methods of preparation are known in the art.

Exemplary relaxing agents include lye, alkali-based, or hydroxide-containing agents which include, but are not limited, to alkali metal hydroxides such as sodium hydroxide, lithium hydroxide, and potassium hydroxide. In some other embodiments, the relaxing agent is ammonium hydroxide. Hydroxide-containing relaxing agents are known to those of skill in the art. Hydroxide-containing relaxers are commercially available, such as from the following commercial brands: Mizani® Rhelaxer, Design Essentials®, and Dudley's Q®.

IV. Kits

Kits for relaxing hair or treating relaxed hair typically contain an active agent formulation containing an effective amount of an active agent.

Instructions for use of the kit are also typically provided.

The kit may further contain a formulation, also referred to herein as the relaxing formulation, capable of disrupting the disulfide bonds in the hair and producing reduced thiol groups during a relaxing process.

The relaxing agent and active agent formulations are typically provided separately and instructions are provided for simultaneously applying the relaxing agent and active agent formulations to the hair. For example, the instructions may provide for creating a mixture of the relaxing agent and active agent formulations, and then applying the mixture to the hair. Alternatively, the instructions may provide for applying the relaxing agent to the hair simultaneously while applying the active agent formulation to the hair (but not as a mixture). The instructions may also include instructions for how to select the desired amount of active agent to be used, such as by specifying a volume or mass (or range thereof) of the active agent or active agent formulation, the desired weight ratio of active agent to relaxing agent, and/or the desired weight ratio of first relaxing formulation to second active agent-containing formulation in order to control the level of curl retention in the relaxed hair.

Alternatively, instructions are provided for first applying the relaxing agent to the hair and subsequently applying the active agent formulation to the hair. The instructions may explain the amount of time (i.e., in the range of about one second to about 30 minutes, more preferably within about 60 seconds) that can pass following the application of the relaxing formulation before the application of the active agent formulation and/or the amount of active agent formulation to be applied in order to control the level of curl retention in the hair. The instructions may also include instructions for how to select the desired amount of active agent to be used, such as by specifying a volume or mass (or range thereof) of the active agent or active agent formulation, the desired weight ratio of active agent to relaxing agent, and/or the desired weight ratio of first relaxing formulation to second active agent-containing formulation in order to control the level of curl retention in the relaxed hair.

A. Relaxing Formulation

In some embodiments, the kit contains a relaxing formulation, which contains one or more relaxing agents for straightening hair as described herein. Hydroxide-containing relaxing agents are well-known to those of skill in the art.

B. Active Agent Formulation

The active agent formulation contains one or more active agents as described herein. Suitable formulations containing the active agents are discussed above. The active agent formulations may be in any suitable form. Suitable forms include, but are not limited to, low to moderate viscosity liquids, lotions, gels, creams, and the like. In certain embodiments, the active agent formulation is a liquid, lotion, or cream of sufficient viscosity which can be mixed with a formulation containing one or more relaxing agents. The active agent formulation is provided in a suitable container, which depends on the form of the formulation.

In one embodiment, the active agent formulation is provided as two or more separate ingredients. For example, the active agent may be provided as a dry powder in a sealed package and the excipient provided in a vial or other container. A suitable mixing container for the active agent and the excipient may be provided.

c. Other Materials in the Kit

The kit may further contain an odor eliminator. The odor eliminator can be incorporated into the reducing formulation. Alternately, the odor eliminator is present in a suitable container for use before or after washing the active formulation from the hair. Suitable odor eliminators are known to those of ordinary skill in the art.

IV. Methods of Use

Methods for treating hair during or immediately following a relaxing process are described herein. In some embodiments, the methods include controlling, selecting, or tuning the level of curl achieved and/or retained during a hair relaxation treatment (with a relaxing formulation) by controlling the relative amount of active agent formulation to the amount of relaxing agent formulation used in a combined formulation containing both components.

In some embodiments, the method for treating hair involves applying a first formulation to the hair containing one or more relaxing agents and applying a second formulation to the hair comprising one or more active agents of Formula I, II, and/or III, as described above.

These methods produce hair with reduced damage or breakage, compared to a treatment of the hair with relaxing agent(s) alone. Further the amount of the one or more active agents of the second formulation is effective to retain a level of curl, which can be expressed as percent curl retention, in the treated hair.

A. Treatment of Hair During or Following a Hydroxide Relaxing Process

The first step in straightening hair is breaking bonds in the hair. The process for breaking the bonds results from the application of a caustic agent. The process for applying a relaxing agent in normal hair straightening procedures is known to those skilled in the art. For example, to relax or straighten hair, the hair is first washed. Second, a formulation containing one or more relaxing agents, such as a sodium hydroxide-containing solution or lotion, is applied to the hair. The hair is allowed to set for a specified period of time, and then the relaxing formulation is rinsed from the hair. Optionally, a neutralizing formulation may be applied to the relaxed hair.

In one embodiment, the active agents described herein can be applied to the hair during the relaxation process. Preferably, the active agent is applied simultaneously with the relaxing agent(s) during the straightening process. In some other embodiments, the active agent can be applied immediately following the application of the relaxing formulation, whether the relaxing formula is rinsed out or not. The active agent formulation is typically applied the same day (i.e. within 24 hours) as the relaxing formulation is applied.

a. Rinse or Wash the Hair

Optionally, the hair may be shampooed and/or conditioned prior to applying the active agent formulation. Alternately, the hair may only be neutralized and/or rinsed with water prior to application of the active agent formulation.

b. Apply the Active Agent Formulation to the Hair

The active agent formulation is applied to the hair either simultaneously during the relaxation process (i.e., in combination with the relaxing agent-containing formulation) or is applied immediately following the application of the relaxing agent formulation or, alternatively, applied at a short interval of time immediately following the application of the relaxing formulation. "Short interval," as used herein, refers to a period of time in the range of one second to 30 minutes, one minute to 20 minutes, or 5 minutes to 15 minutes. In certain other embodiments, the active agent formulation is applied within the same day following application/treatment of the hair with the relaxing formulation.

In some embodiments, a first formulation containing one or more relaxing agent(s) and a second formulation containing one or more active agent(s) are combined, mixed and applied to the hair as a single combined formulation containing both types of agents to the hair undergoing a relaxing/straightening process. In some embodiments, the weight ratio of relaxing agent(s) to active agent(s) in the combined formulation is selected to control and retain a particular level of curl, which can be expressed as percent curl retention, in the hair as compared to the hair's unrelaxed (e.g. natural) amount of curl. Typically, the lower the amount of active agent(s) relative to the amount of relaxing agents the greater the extent of straightening. Conversely, the higher the amount of active agent(s) to relaxing agent(s) present in the combined formulation the greater the level of retention of curl. Similarly, in other embodiments, the level of curl retained in the treated hair is determined by the amount of the active agent(s) present in the second formulation, where the amount of active agent(s) used is lower for a lower percentage of curl retention than the amount of active agent(s) used for a higher percentage of curl retention. Accordingly, it is possible to tune the level of curl retained in hair that is treated with lye or alkali-based relaxing agents or hydroxide-containing relaxing agents by applying a selected amount of the one or more active agent(s).

In some embodiments, the weight ratio of the first formulation containing relaxing agent(s) to the second formulation containing active agent(s) is in the range of about 1:99 to about 99:1, more preferably about 10:1 to about 1:10 and the weight ratio is effective to retain a level of the hair's unrelaxed and natural curl (i.e. before relaxing treatment). The weight ratio may be about 10:1, 9:1, 8:1, 7:1, 6:1, 5:1, 4:1, 3:1, 2:1 or 1:1 of the first formulation to the second formulation. In some preferred embodiments, the weight ratio of the first formulation to the second formulation is 8:1. In other preferred embodiments, the weight ratio of the first formulation to the second formulation is 4:1. These ratios are particularly useful with commercially available relaxing agents, such as Mizani® Rhelaxer, as shown in the Examples. The amount of the second formulation containing active agent(s) and the concentration of the active agent(s) present therein can be varied as needed when using other relaxing agents to achieve similar results. Commercially available hydroxide-based relaxer formulations typically have a pH of about 12 to 14, representing a difference in hydroxide ion concentration of about 100 times between the ends of the range. Thus, the amount of active agent(s) can be varied as a function of the pH of the relaxing formulation being used, and can be further adjusted according to the buffering capacity of each relaxer, if a buffering agent is present.

In yet other embodiments, the weight ratio of the first formulation containing relaxing agent(s) to the weight of active agent(s) is in the range of about 1:99 to about 99:1, more preferably about 10:1 to about 1:10 and the weight ratio is effective to retain a level of the hair's unrelaxed and natural curl (i.e. before relaxing treatment). In some preferred embodiments, the weight ratio of the first formulation to the weight of the active agent(s) is 40:1. In other preferred embodiments, the weight ratio of the first formulation to the weight of the active agent(s) is 20:1.

As used herein, "percent curl retention" and "percentage of curl retention" are used interchangeably to refer to the level of curl that is retained following a treatment, as compared to the hair's unrelaxed and natural amount of curl (i.e. prior to treatment with a relaxing agent). One exemplary method for determining percent curl retention of treated hair (e.g. a swatch of hair) is based on the following calculation using the formula:

$$\text{Percent Curl Retention} = (L_{ext} - L_f)/(L_{ext} - L_i) \times 100$$

where $L_{ext}$ is the length of hair prior to treatment when fully extended, $L_f$ is the final (non-extended) length of the hair following a treatment, and $L_i$ is the initial (non-extended) length of hair in its initial (i.e. unrelaxed) state with its natural amount of curl, and where $L_{ext}$ does not equal $L_i$. For example, the level of curl (percent curl retention) to be retained following treatment with the active agent(s) and relaxing agent(s) can be in the range of about 0-99%, more preferably less than about 90%, more preferably less than about 80%, more preferably less than about 70%, more preferably less than about 60%, more preferably less than about 50%. In certain embodiments, the level of curl retained is between 0% and 10%. In other embodiments, the percent curl retention is greater than 50%.

In embodiments where the hair is straightened with little to no curl remaining in the hair, the level of curl retaining is less than about 10%, such as from about 10% to 0%, from about 5% to 0%, or from about 1% to 0%.

The percent of curl retention of the hair following treatment can be maintained with no appreciable or substantially (i.e., less than about 5%, 4%, 3%, 2%, or 1%) no appreciable change in its level of curl for a period of time in the range of one week to six months, more preferably two weeks to four months, and most preferably one month to three months. In some embodiments, the percentage of curl retention can be maintained for at least about one week, two weeks, three weeks, four weeks, one month, two months, three months, four months, five months, six months, or longer.

In some embodiments, the active agent-containing second formulation is is applied to the hair immediately after the application of a first relaxing agent-containing formulation, while in other embodiments a short interval of time is permitted to pass prior to application of the active agent containing formulation (e.g. 10, 15, 25, 30, 45, or 60 seconds or longer following relaxing formulation application). The hair being treated does not have to be washed or rinsed prior to the application of the active agent containing formulation. In some embodiments, the intervening period of time between the application of the relaxing agent(s) and the subsequent application of the active agent formulation and/or the amount of active agent formulation applied to the relaxing hair can be used to control the percent curl retention in the relaxed hair. In some embodiments, the amount of time between the application of the relaxing agent containing formulation and the application of the active agent containing formulation can be selected to achieve a desired amount or range of percent curl retention.

In some embodiments, the active agent formulation may be applied in a single application, or application may be repeated one or more times as needed. Typically, the amount of active agent formulation applied is sufficient to saturate the hair. The volume of active formulation applied to the hair in each application may be about 1 to about 100 mL per person depending on their length and volume of hair. In some embodiments, application of the active agent can be repeated immediately (e.g. within about 10 to 15 seconds) or between about one and five minutes, greater than five minutes, between about five and ten minutes, greater than ten minutes, between about ten and twenty (20) minutes after the initial application of the active agent formulation.

The active agent formulations described herein which are applied in combination with relaxing agent(s) or immediately subsequent to the application of a hair relaxing treatment can improve hair quality, such as appearance (e.g., sheen) and feel, increase wet and dry strength, and decrease hair breakage when the hair is subjected to subsequent treatments, such as coloring.

In some embodiments, hair breakage can be decreased by 5, 10, 15, 20, 25, 30, 35, 40, 45, 50, 55, 60, 65, 70, or 75% or higher after treatment with the active agent, as compared to relaxed hair excluding the use of an active agent formulation. Hair breakage is a significant problem encountered during typical hair relaxing treatments.

c. Remove the Relaxing and/or Active Agent Formulation from the Hair

The treated hair can be washed, rinsed, shampooed, or conditioned subsequent to the relaxing process including the application of an active agent formulation. The hair may be rinsed and subsequently washed immediately (e.g. within 10, 15, 25, 30, 45, 60 seconds (one minute), two minutes, three minutes, four, or five minutes following application) after application of the active agent-containing formulation. Alternatively the hair may be rinsed, shampooed, or conditioned within about 60 minutes following application of the first and second formulations, within about 45 minutes following application, between about 5 minutes and about 20 minutes, or about 10 minutes after the final application of the active agent formulation to the hair, depending on the hair type. In some embodiments of the methods described herein, the treated hair is washed, rinsed, shampooed, or conditioned about 45 minutes after the application of the relaxing and active agent formulations, when they are applied simultaneously. In some embodiments of the methods described herein, the treated hair is washed, rinsed, shampooed, or conditioned about 15 minutes after the application of an active agent formulation, when the active formulation is applied immediately (i.e., within about 5, 10, 15, 20, 25, 30, 35, 40, 45, 50, 55, 60 seconds (one minute), two minutes, three minutes, four, or five minutes) after applying the relaxing agent formulation.

Alternately, the hair may be washed, rinsed, shampooed, or conditioned and a subsequent application of the active agent formulation may be applied which does not have to be washed or rinsed from the hair.

The active agent(s) can covalently react with thiols present in the relaxed hair and the thiols remain crosslinked for at least one week, preferably for at least one month following application of the active agent. The thiols may remain crosslinked for longer periods of time, such as for about three months or greater than three months, such as for at least one year following application of the active agent. The reaction is a stable reaction, such that the thiols remain crosslinked even if subjected to a hair coloring treatment (simultaneous or subsequent to the relaxing process).

EXAMPLES

Example 1: Controlled Relaxing of Hair Using Bismaleate Active Agent in Combination With a Hydroxide-Containing Relaxer General Hair samples were obtained from a human subject and cut in ½ inch wide wefts.

Relaxing agents: Mizani® Rhelaxer normal strength.

Active agent-containing relaxing formulation: One ounce of the commercial hydroxide formulation was further mixed with a liquid solution containing 0.25 ounces of a formulation having 20 weight percent of 2,2'-(ethane-1,2-diylbis(oxy))bis(ethan-1-amine) di-maleate as the active agent.

Methods

The active agent-containing relaxation formulation was brushed into the hair sample and left for 45 minutes with periodic combing. The solution was subsequently washed with shampoo, conditioned, and allowed to dry.

Results

The combination of the active agent and hydroxide (lye) relaxer produced relaxed hair that had more curl than a control (relaxing formulation which contains no active agent). The appearance and texture of the relaxed hair treated with a combination of the lye-based relaxing agent and active agent formulation demonstrated much improved hair conditioning (stronger, improved feel, softer with lower porosity), as compared to the control.

Example 2: Controlled Relaxing of Hair Using Bismaleate Active Agent in Combination With a Hydroxide-Containing Relaxer General Hair samples were obtained from a human subject and cut in ½ inch wide wefts.
Relaxing agents: Mizani® Rhelaxer normal strength.
Active agent-containing relaxing formulation: One ounce of the commercial hydroxide formulation was further mixed with a liquid solution containing 0.125 ounces of a formulation having 20 weight percent of 2,2'-(ethane-1,2-diylbis(oxy))bis(ethan-1-amine) di-maleate as the active agent.

Methods

The active agent-containing relaxation formula was brushed into the hair sample and left for 45 minutes with periodic combing. The hair was then washed with shampoo, conditioned, and allowed to dry.

Results

As compared to the formulation tested in Example 1, the combination of the active agent and hydroxide (lye) relaxer but which contained a reduced amount of the active agent produced relaxed hair that had less curl than in Example 1, but had more curl as compared to a control (relaxing agent which contains no active agent).
The appearance and texture of the relaxed hair treated with a combination of the lye-based relaxing agent and active agent formulation demonstrated much improved hair conditioning (stronger, improved feel, softer with lower porosity), as compared to the control.

Example 3: Controlled Relaxing of Hair Using Maleic Acid as the Active Agent in Combination With a Hydroxide-Containing Relaxer General Hair samples were obtained from a human subject and cut in ½ inch wide wefts.
Relaxing agents: Mizani® Rhelaxer normal strength.
Active agent-containing relaxing formulation: One ounce of the commercial hydroxide formulation was further mixed with a liquid solution containing 0.25 ounces of a formulation having 10 weight percent of maleic acid as the active agent.

Methods

The active agent-containing relaxation formulation was brushed into the hair sample and left for 45 minutes with periodic combing. The solution was subsequently washed with shampoo, conditioned, and allowed to dry.

Results

The combination of the active agent and hydroxide (lye) relaxer resulted in relaxed hair that had more curl than a control (relaxing formulation that contained no active agent). The appearance and texture of the relaxed hair treated with a combination of the lye-based relaxing agent and active agent formulation demonstrated much improved hair conditioning (stronger, improved feel, softer with lower porosity), as compared to the control.

Example 4: Treating Lye Relaxed Hair Using a Bismaleate Active Agent

General

Hair samples were obtained from a human subject and cut in ½ inch wide wefts.
Relaxing agents: Mizani® Rhelaxer normal strength.
Active agent formulation: A 0.5 ounce formulation of 20 weight percent of 2,2'-(ethane-1,2-diylbis(oxy))bis(ethan-1-amine) di-maleate as the active agent was prepared in water (3 ounces).

Methods

The commercial relaxation formula was brushed into the hair sample and left for 45 minutes with periodic combing. The hair was then washed with shampoo, conditioned, and allowed to dry.
The active agent formula was then applied to the dried, relaxed hair and allowed to stand for 15 minutes. The hair was then washed with shampoo, conditioned, and allowed to dry.

Results

The appearance and texture of hair which was first treated with a lye-based relaxing agent and subsequently treated with an active agent formulation demonstrated much improved hair conditioning (stronger, improved feel, with lower porosity), as compared to the control. After the treatment, some of the original curl returned to the hair as compared to the hair immediately after lye-relaxation without the use of an active agent.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:
1. A kit comprising:
(a) a first formulation comprising one or more relaxing agents and having an alkaline pH, and
(b) a second formulation comprising an active agent, wherein the active agent has the following structure:

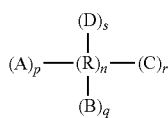

Formula I wherein
A, B, C, and D are reactive moieties containing one or more charges, and wherein each of A, B, C, and D independently contains a moiety selected from the group consisting of a vinyl sulfone, an acrylate group, a methacrylate group, a styrene group, an acryl amide group, a methacryl amide group, a maleate group, a fumarate group, and an itaconate group;
R is a linker that contains two or more charges, wherein the charges are opposite to the charges on the reactive moieties, wherein n=1-10, and wherein R is not a polymer, and
wherein the sum of the charges is zero;
wherein the reactive moieties are ionically bound to the linker; and
wherein each occurrence of p, q, r, and s is independently an integer from 0 to 25,
wherein the sum of p+q+r+s is equal to or greater than 2.

2. The kit of claim 1, wherein the linker is a polyfunctional molecule, wherein the linker is optionally independently substituted with one or more substituents selected from the group consisting of hydrogen, halogen, cyano, alkoxy, alkyl, alkenyl, cycloalkyl, cycloalkenyl, aryl, heterocycloalkyl, heteroaryl, amine, hydroxy, formyl, acyl, carboxylic acid, —C(O)R$^1$, —C(O)OR$^1$, carboxylate, primary amide, secondary amide, —C(O)NR$^1$R$^2$, —NR$^1$R$^2$, —NR$^1$S(O)$_2$R$^2$, —NR$^1$C(O)R$^2$, —S(O)$_2$R$^2$, —SR$^1$, and —S(O)$_2$NR$^1$R$^2$, sulfinyl group, and sulfonyl group; wherein R$^1$ and R$^2$ may each independently be hydrogen, alkyl, alkenyl, alkynyl, cycloalkyl, aryl, heterocycloalkyl, or heteroaryl; wherein each of R$^1$ and R$^2$ is optionally independently substituted with one or more substituents selected from the group consisting of halogen, hydroxyl, cyano, nitro, amino, alkylamino, dialkylamino, alkyl optionally substituted with one or more halogen or alkoxy or aryloxy, aryl optionally substituted with one or more halogen or alkoxy or alkyl or trihaloalkyl, heterocycloalkyl optionally substituted with aryl or heteroaryl or =O or alkyl optionally substituted with hydroxyl, cycloalkyl optionally substituted with hydroxyl, heteroaryl optionally substituted with one or more halogen or alkoxy or alkyl or trihaloalkyl, haloalkyl, hydroxyalkyl, carboxy, alkoxy, aryloxy, alkoxycarbonyl, aminocarbonyl, alkylaminocarbonyl, and dialkylaminocarbonyl.

3. The kit of claim 1, wherein the linker is a polyfunctional molecule, and wherein the linker is an alkoxy, an ether, an alkyl, an alkenyl, a cycloalkyl, a cycloalkenyl, an aryl, a heterocycloalkyl, a heteroaryl, or an amine.

4. The kit of claim 1, wherein the one or more relaxing agents are alkali metal containing hydroxides selected from the group consisting of sodium hydroxide, lithium hydroxide, and potassium hydroxide.

5. The kit of claim 1, wherein the second formulation is in the form of a liquid.

6. The kit of claim 1, wherein the second formulation is in the form of a cream.

7. The kit of claim 1, wherein the second formulation is in the form of a lotion.

8. The kit of claim 1, wherein the second formulation is in the form of a gel.

9. The kit of claim 1, wherein the active agent is:

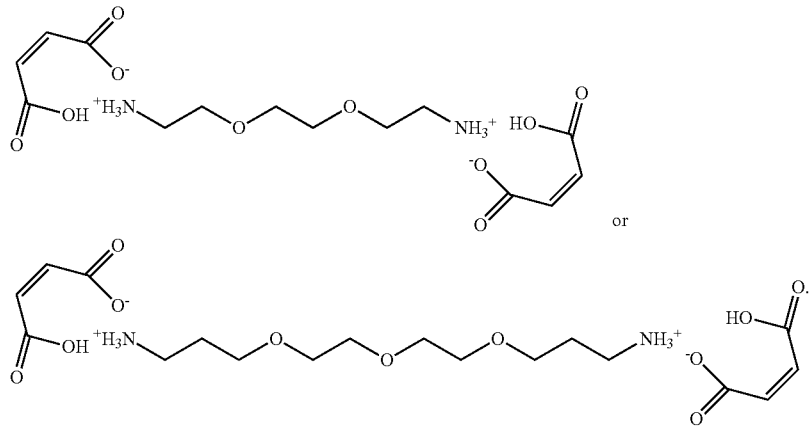

10. The kit of claim 1, wherein the second formulation further comprises one or more cosmetically acceptable excipients selected from the group consisting of water, surfactants, vitamins, natural extracts, preservatives, antioxidants, chelating agents, proteins, amino acids, humectants, fragrances, emollients, penetrants, thickeners, viscosity modifiers, hair fixatives, film formers, emulsifiers, opacifying agents, propellants, liquid vehicles, carriers, salts, pH adjusting agents, neutralizing agents, buffers, hair conditioning agents, anti-static agents, anti-frizz agents, anti-dandruff agents, and combinations thereof.

11. The kit of claim 10, wherein the cosmetically acceptable excipient is present in an amount ranging from about 40 wt % to about 99 wt % of the second formulation.

12. The kit of claim 1, wherein the active agent is present in an amount ranging from about 1 wt % to about 25 wt % of the second formulation.

13. The kit of claim 12, wherein the active agent is present in an amount ranging from about 1 wt % to about 15 wt % of the second formulation.

14. The kit of claim 12, wherein the active agent is present in an amount ranging from about 1 wt % to about 10 wt % of the second formulation.

15. The kit of claim 12, wherein the active agent is present in an amount ranging from about 1 wt % to about 5 wt % of the second formulation.

16. The kit of claim 1, further comprising instructions for use, a mixing container, an odor eliminator, or a combination thereof.

17. The kit of claim 1, wherein the second formulation is provided as two or more separate ingredients.

18. The kit of claim 17, wherein the binding agent is provided as a dry powder in a sealed package and a cosmetically acceptable excipient is provided in a vial or other container.

\* \* \* \* \*